(12) United States Patent
Ghosh et al.

(10) Patent No.: US 7,858,763 B2
(45) Date of Patent: Dec. 28, 2010

(54) TRANSFORMING GROWTH FACTOR BETA 1 (TGFβ1) HAPLOTYPES AND PREDICTION OF SUSCEPTIBILITY FOR IMMUNOLOGICAL DISORDERS

(75) Inventors: Balaram Ghosh, New Delhi (IN); Shilpy Sharma, New Delhi (IN); Kamalpreet Nagpal, New Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 512 days.

(21) Appl. No.: 11/146,381

(22) Filed: Jun. 6, 2005

(65) Prior Publication Data

US 2006/0024706 A1 Feb. 2, 2006

(30) Foreign Application Priority Data

Jun. 4, 2004 (IN) .................. 1037/DEL/2004

(51) Int. Cl.
*C07H 21/02* (2006.01)
*C07H 21/04* (2006.01)
*C12Q 1/68* (2006.01)

(52) U.S. Cl. .................. 536/23.1; 536/23.5; 435/6
(58) Field of Classification Search .................. None
See application file for complete search history.

(56) References Cited

U.S. PATENT DOCUMENTS 4,683,202 A   7/1987   Mullis

FOREIGN PATENT DOCUMENTS

| EP | 0 235 726 | 9/1987 |
|---|---|---|
| WO | WO-89/11548 | 11/1989 |
| WO | WO-93/22456 | 11/1993 |
| WO | WO-02/08468 | 1/2002 |

OTHER PUBLICATIONS

Hacker UT et al 'Lack of association between an interleukin-1 receptor antagonist gene polymorphism and ulcerative colitis.' Gut. May 1997;40(5):623-7.*
Juppner H 'Functional properties of the PTH/PTHrP receptor.' Bone. Aug. 1995;17(2 Suppl):39S-42S.*
Kang D et al 'Lack of association of transforming growth factor-beta1 polymorphisms and haplotypes with prostate cancer risk in the prostate, lung, colorectal, and ovarian trial.' Cancer Epidemiol Biomarkers Prev. Jun. 2007;16(6):1303-5.*
Heinzmann A et al 'Polymorphisms of the TGF-beta1 gene are not associated with bronchial asthma in Caucasian children.' Pediatr Allergy Immunol. Jun. 2005;16(4):310-4.*
Grothues D. et al 'PCR amplification of megabase DNA with tagged random primers (T-PCR).' Nucleic Acids Res. Mar. 1993 11;21(5):1321-2.*
Nagpal K et al 'TGFbeta1 haplotypes and asthma in Indian populations.' J Allergy Clin lmmunol. Mar. 2005;115(3):527-33.*
Quarmby S. et al. int. j. radiat. biol (2003), vol. 79, No. 2, 137-143.*
Seki M. et al. DNA Research (1996) vol. 3, pp. 107-108.*
Abney et al., Am. J. Hum. Genet., 70:920-934 (2002).
Accession No. AC011462.
Accession No. BV209662.
Alam et al., J. Exp. Med., 179:1041-1045 (1994).
Barnes, Respir. Res., 2:64-65 (2001).
Ben-Asouli et al., Cell, 108:221-232 (2002).
Bleecker et al., Am. J. Respir. Crit. Care Med., 156:S113-S116 (1997).
Chang et al., Proc. Natl. Acad. Sci. USA, 85:6856-6860 (1988).
Cohen et al., Proc. Natl. Acad. Sci. USA, 81:1774-1778 (1984).
de Gouyon et al., Proc. Natl. Acad. Sci. USA, 90:1877-1881 (1993).
Dunning et al., Cancer Res., 63:2610-2615 (2003).
Elias et al., J. Clin. Invest., 104(8):1001-1006 (1999).
Grainger et al., Hum. Mol. Genet., 8(1):93-97 (1999).
Hansen et al., J. Clin. Invest., 105(1):61-70 (2000).
Hefferon et al., Proc. Natl. Acad. Sci. USA, 101(10):3504-3509 (2004).
Hill et al., Am. J. Respir. Cell Mol. Biol., 21:728-737 (1999).
Hirschhorn et al., Proc. Natl. Acad. Sci. USA, 97(22):12164-12169 (2000).
Hobbs et al., Am. J. Respir. Crit. Care Med., 158:1958-1962 (1998).
Holbert et al., Proc. Natl. Acad. Sci. USA, 98(4):1811-1816 (2001).
Julier et al., Proc. Natl. Acad. Sci. USA, 87:4585-4589 (1990).
Kreutz et al., Proc. Natl. Acad. Sci. USA, 92:8778-8782 (1995).
Kwoh et al., Proc. Natl. Acad. Sci. USA, 86:1173-1177 (1989).
Lander et al., Proc. Natl. Acad. Sci. USA, 83:7353-7357 (1986).
Lathrop et al., Proc. Natl. Acad. Sci. USA, 81:3443-3446 (1984).
Longo et al., Tob. Control, 10:267-272 (2001).
Mattila et al., Nucleic Acids Res., 19(18):4967-4973 (1991).
Minshall et al., Am. J. Respir. Cell Mol. Biol., 17:326-333 (1997).
Mokdad-Gargouri et al., Nucleic Acids Res., 29(5):1222-1227 (2001).
Nakao et al., J. Exp. Med., 192(2):151-158 (2000).
Ober et al., Am. J. Hum. Genet., 67:1154-1162 (2000).
Oberle et al., Proc. Natl. Acad. Sci. USA, 83:1016-1020 (1986).
Orita et al., Proc. Natl. Acad. Sci. USA, 86:2766-2770 (1989).
Redington et al., Am. J. Respir. Crit. Care Med., 156:642-647 (1997).
Reich et al., Nature, 411:199-204 (2001).
Rothenburg et al., Proc. Natl. Acad. Sci. USA, 98(16):8985:8990 (2001).
Sachidanandam et al., Nature, 409:928-933 (2001).
Sherman et al., J. Immunol., 162:2703-2708 (1999).
Shrivastava et al., Nucleic Acids Res., 22(24):5151-5155 (1994).

(Continued)

*Primary Examiner*—Stephen Kapushoc
(74) *Attorney, Agent, or Firm*—Marshall, Gerstein & Borun LLP

(57) ABSTRACT

The present invention is related to the haplotypes of human Transforming Growth Factor Beta1 (TGFβ1) and prediction of susceptibility for immunological disorders. More particularly the present study is the first study in any population, identifying novel protective and risk haplotypes of the TGFβ1 gene The present invention also relates to allelic variants of the human Transforming Growth Factor Beta1 (TGFβ1) gene. The said invention also provides primers and methods suitable for the detection of these haplotypes and allelic variants for the prediction of an individual's disease susceptibility, and/or the genetic analysis of the TGFβ1 gene for immunological disorders, particularly asthma. A vital aspect of the present study provides a method for predicting susceptibility of individuals to immunological disorders, particularly asthma.

10 Claims, 2 Drawing Sheets

OTHER PUBLICATIONS

Figure 1:
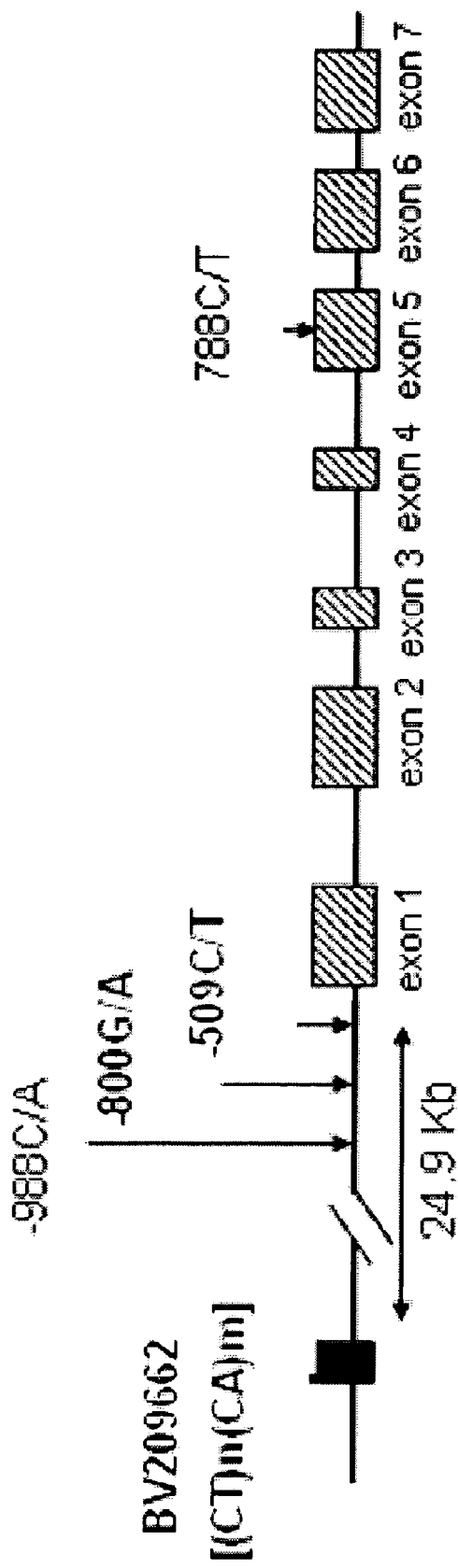

Silverman et al., Am. J. Respir. Crit. Care Med., 169(2):214-219 (2004).
Stephens et al., Am. J. Hum. Genet., 68:978-989 (2001).
Stephens et al., Am. J. Hum. Genet., 73(5):1162-1169 (2003).
Texereau et al., Thorax, 59:156-158 (2004).
Thomas et al., Am. J. Respir. Crit. Care Med., 156:S144-S151 (1997).
Xu et al., Am. J. Hum. Genet., 68:1437-1446 (2001).
Zuany-Amorim et al., Nat. Med., 8(6):625-629 (2002).

* cited by examiner

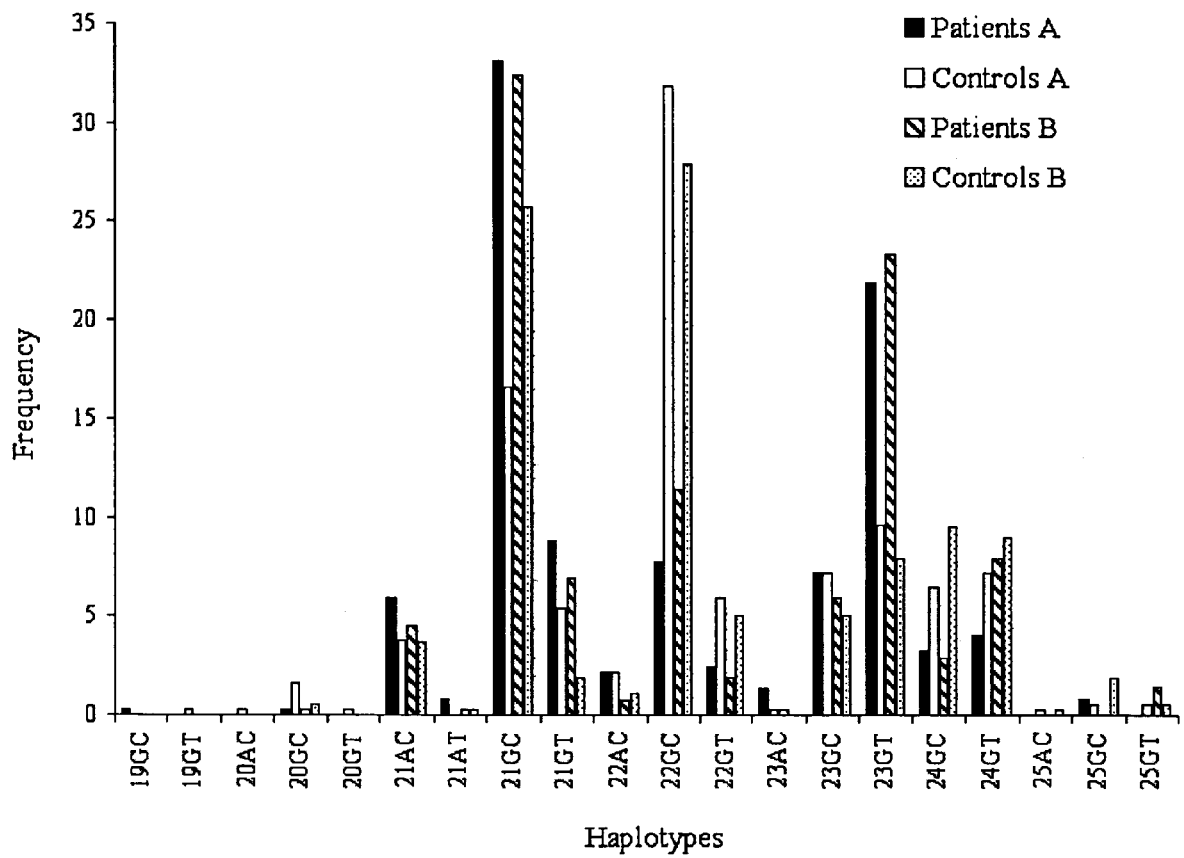
Figure 2: The frequency distribution of the haplotypes of the *TGFβ1* gene in patients and unrelated controls in cohorts A and B, respectively. The haplotypes were plotted on the X-axis and their respective relative frequencies (%) on the Y-axis.

TRANSFORMING GROWTH FACTOR BETA 1 (TGFβ1) HAPLOTYPES AND PREDICTION OF SUSCEPTIBILITY FOR IMMUNOLOGICAL DISORDERS

The present application claims the benefit of priority under 35 U.S.C. Section 119 for Indian Application No. 1037/DEL/204, which was filed Jun. 4, 2004. The entire text of the aforementioned priority application is incorporated herein by reference.

FIELD OF INVENTION

The present invention is related to the haplotypes of human Transforming Growth Factor Beta1 (TGFβ1) and prediction of susceptibility for immunological disorders. More particularly the present study is the first study in any population, identifying novel protective and risk haplotypes of the TGFβ1 gene The present invention also relates to allelic variants of the human Transforming Growth Factor Beta1 (TGFβ1) gene. The said invention also provides primers and methods suitable for the detection of these haplotypes and allelic variants for the prediction of an individual's disease susceptibility, and/or the genetic analysis of the TGFβ1 gene for immunological disorders, particularly asthma. A vital aspect of the present study provides a method for predicting susceptibility of individuals to immunological disorders, particularly asthma.

BACKGROUND INFORMATION

The genomic DNA of all organisms undergoes spontaneous changes in the sequence (termed as mutation) in the course of their continuing evolution thereby generating variant forms of progenitor sequences, which may lead to various evolutionary advantages or disadvantages to the survival of the organism. If such effects of the mutations or variations are not seen then they are termed as neutral changes/mutations. If the mutation is lethal then it is not transmitted to the following generations and thus is lost from the gene pool of that organism. A variant form may also confer an evolutionary advantage to the species and is eventually incorporated into the DNA of many or most members of the species, and hence, effectively it becomes the progenitor form. In many instances, both progenitor and variant form(s) survive and co-exist in the gene pool of the species. This coexistence of multiple forms of a sequence gives rise to polymorphisms.

Several different types of polymorphism have been reported. A restriction fragment length polymorphism (RFLP) means a variation in DNA sequence that alters the length of a restriction fragment. The restriction fragment length polymorphism may create or delete a restriction site, thus changing the length of the restriction fragment. RFLPs have been widely used in human and animal genetic analyses. Other polymorphisms take the form of short tandem repeats (STRs) that include tandem di-, tri- and tetranucleotide repeated motifs. These tandem repeats are also referred to as variable number tandem repeat (VNTR) polymorphisms. VNTRs have been used in identity and paternity analysis and in a large number of genetic mapping studies. Other polymorphisms take the form of single nucleotide variations. Such polymorphisms are far more frequent than RFLPS, STRs and VNTRs. Some single nucleotide polymorphisms (SNPs) occur in protein-coding sequences, in which case, one of the polymorphic forms may give rise to the expression of a defective or other variant protein and, potentially, a genetic disease. Examples of genes, in which polymorphisms within coding sequences give rise to genetic disease include beta.-globin (sickle cell anemia) and CFTR (cystic fibrosis). Other single nucleotide polymorphisms occur in noncoding regions. Some of these polymorphisms may also result in defective protein expression (e.g., as a result of defective splicing). Other single nucleotide polymorphisms have no phenotypic effects.

The effects of such polymorphisms can be at various levels of cellular organization. Polymorphic elements in the promoter and/or regulatory regions are known to modulate the levels of mRNA of the genes. Polymorphisms in the untranslated regions (UTR's) of the RNA have also been documented to regulate the transcriptional and translational rates of the genes. Their presence in the intron-exon boundaries can also lead to changes in splicing and or splice products that are formed from the native full length mRNA. Polymorphisms in the coding region may change the function of the protein if it is a non-synonymous change and if it occurs in a critical domain of the protein leading to functional changes of the protein.

Thus polymorphisms are useful in defining genomic regions (for example as genetic markers) and they may also lead to disease (for example functional polymorphisms). Numerous examples are documented in the scientific literature and persons trained in this field are familiar with it (please see Abney M et al, Am J Hum Genet 70:920-34, 2002; Baron M, Mol Psychiatry 6:143-9, 2001; Bodmer W F, Ciba Found Symp 130:215-28, 1987; Breslow J L, Physiol Rev 68:85-132, 1988; Caraballo L R and Hernandez M, Tissue Antigens 35:182-6, 1990; Levitt R C, Am J Respir Crit Care Med 150:S94-9, 1994; Xu J et al, Clin Exp Allergy 28 Suppl 5:1-5; discussion 26-8, 1998).

Atopic diseases are a clinically heterogeneous group of diseases characterized by elevated serum IgE levels and varying phenotypic expressions such as Asthma and Atopic Dermatitis (Barnes K C, Clin Exp Allergy 29 Suppl 4:47-51 1999; Barnes P J, Respir Res 2:64-5, 2001; Blumenthal M N and Amos D B, Chest 91:176S-184S, 1987; Thomas N S et al, Am J Respir Crit Care Med 156:S144-51, 1997). Specifically, Asthma is a chronic airway disease, affecting 15-18% of the world's population. It is mainly a childhood disorder though the age of onset can vary and is seen to be 35-45 yr. in the general population. Another case of extrinsic asthma is observed where the age of onset is above 45 yr. and is mainly due to the age induced changes in the lung function. The pathophysiology of atopic asthma is well documented. It is a T helper type 2 (Th2) mediated disorder with cytokines such as interleukin-4, interleukin-5, interleukin-13, implicated in the deviation of the immune system towards atopicity. Increased levels of these cytokines lead to elevated total serum IgE levels, eosinophil recruitment, and bronchial hyper-responsiveness that ultimately culminate in asthma pathogenesis. These interleukins are also known to interact and stimulate the alveolar cells and bronchial smooth muscle cells resulting in the clinical phenotypes of bronchial hyper-responsiveness (Barnes P J, Respir Res 2:64-5, 1999). Gene-gene and gene-environment interactions have been implicated in the development of asthma (Tay et al, Asian Pac J Allergy Immunol 17:239-42, 1999; Bleecker E R, Am J Respir Crit Care Med 156:S113-6, 1997; Cookson W, Nature, 402:B5-11, 1999).

Although inflammation is undoubtedly a cornerstone of asthma, the structural changes associated with asthma with respect to the cells and tissues of the airways have escaped the importance deserved. These structural changes are collectively given the term "Airway Remodeling" and the complex picture of asthma would be incomplete without giving this aspect its due relevance.

Various genetic studies have shown multiple loci to be associated with the disease. Asthma is therefore a multigenic disorder with a number of genes contributing minor effects leading to pathogenesis. Linkage studies, in various populations, have narrowed down the presence of susceptibility or disease genes to chromosomal locations such as 1p31, 5q31-33, 11p13, 12q13-24, 13q14, 17q12-21. However, all the causative genes and mutations have so far not been identified (Bleeker E R et al, Am J Respir Crit Care Med 156:S113-6, 1997; Blumenthal M N, Chest 91:176S-184S, 1987, Duffy D L, Epidemiol Rev 19:129-43, 1997). Recent advances in genome wide scans have identified several chromosomal regions such as 11q, 10p, 20p, 5q, 8p, 12p, 14q to be associated with asthma/atopy (Blumenthal M N et al, Hum Genet 114(2):157-164, 2004). Also a study has linked chromosomes 19, 20, 3, 12, 18, 11, 13 to mite sensitivity, which is a major risk factor for asthma (Blumenthal M N et al, Genes Immun 5(3): 226-231, 2004)

Transforming growth factor beta 1 (TGFβ1) plays an important role in airway wall remodeling, an established pathological feature in asthma (Elias et al, J Clin Invest 104: 1001-1006, 1999; Redington et al, Am J Respir Crit Care Med 156:642-647, 1997). It is implicated in several aspects of fibrosis (Minshall et al, Am J Respir Cell Mol Biol 17:326-333, 1997) wherein subepithelial fibrosis is increased in severe asthmatics (Massague, Annu Rev Cell Biol 6:597-641, 1990). In addition, it decreases synthesis of enzymes that degrade the ECM (extracellular matrix), such as collagenase and stromelysin, and increases synthesis of inhibitors of these enzymes, including tissue inhibitor of metalloprotienase-1 (TIMP-1) and plasminogen activator inhibitor type-1 (PAI-1) (Massague, Annu Rev Cell Biol 6:597-641, 1990). TGFβ1 mRNA levels in eosinophils are increased in patients with severe asthma as compared to mild asthma (Minshall et al, Am J Respir Cell Mol Biol 17:326-333, 1997, Ohno et al, Am J Respir Cell Mol Biol 15:404-409, 1996). Alternatively, it prevents the development of allergic inflammation through the capacity to inhibit IgE synthesis and through inhibition of basophil and eosinophil proliferation (Taylor et al, Int Arch Allergy Immunol 135(1):73-82, 2004). Additionally, it abrogates the survival effects of hematopoietins on eosinophils and thereby induces their apoptosis (Alam et al, J Exp Med 179:1041-1045, 1.994). This complex mix of pro- and anti-inflammatory activities make TGFβ1 a promising candidate gene for asthma.

The TGFβ1 gene is located on chromosome 19q13.1-13.2 (Fujii et al, Somat Cell Mol Genet; 12:281-288) and has recently been linked to mite sensitivity (Blumenthal et al, Genes Immun 5:226-231, 2004). Studies carried out in different populations have identified various polymorphisms, such as −988C/A, −800G/A, −509C/T, 869T/C and, 915G/C. Earlier studies also reported a strong linkage disequilibrium (LD) between −509C/T, 869T/C and 915G/C (Dunning et al, Cancer Res 63(10):2610-2615, 2003; Pulleyn et al, Hum Genet. 109:623-627, 2001). Out of these SNPs, the C to T transition at −509 position has been found to be associated with elevated IgE levels (Hobbs et al, Am J Respir Crit Care Med 158:1958-1962, 1998) and TGFβ1 levels (Grainger et al, Hum Mol Genet 8:93-97, 1999). In another study, this polymorphism was associated with asthma severity (Pulleyn et al, Hum Genet 109:623-627, 2001). In the same study, four other polymorphisms, −988C/A, −800G/A, 869T/C and 915G/C were assessed for association with asthma but no significant association was found. A similar study in the Czech population showed no association with asthma (Buckova et al, Allergy 56:1236-1237, 2001).

Thus, both genetic and biochemical evidence indicate that TGFβ1 is a potential candidate gene for disease pathogenesis and/or susceptibility to disorders including asthma. To elucidate its genetic role in asthma, we have carried out a case-control study in two independent cohorts of asthma patients and controls (Nagpal et al, J Allergy Clin Immunol. 115(3): 527-33, 2005). Here, we have genotyped a novel repeat (Accession number BV209662) and two SNPs, viz. −800G/A and the −509C/T, encompassing a region of 24.7 Kb and have analyzed the association of these polymorphisms independently and at the level of haplotype with asthma and also with serum TGFβ1 levels.

Moreover, there is evidence to suggest that ethnic differences exist in the susceptibility genes associated with asthma (Xu J et al, Am J Hum Genet 68:1437-46, 2001). Chromosome 19q13.1-13.2 harbors the Transforming Growth Factor Beta1 (TGFβ1) gene (consisting of 7 exons spanning a region of 23 kbp) (Fujii D et al, Somat. Cell Mol. Genet. 12:281-288, 1986). This gene mediates a complex mix of pro- and anti-inflammatory activities. Like IL-10, TGFβ1 indirectly inhibits T-cell activation by modulation of antigen presenting cell function and deactivating macrophages (Tsunawaki S et al, Nature 334:260-262, 1998). It also prevents the development of allergic inflammation through a capacity to inhibit IgE synthesis and through inhibition of mast cell proliferation. Additionally, it abrogates the survival effects of hematopoietins on eosinophils and thereby induces their apoptosis (Alam R et al, J Exp Med 179:1042-1045, 1994). It has also been shown that T cells engineered to secrete TGFβ1, in contrast to INF-γ secreting Th1 cells, could very effectively reduce airway inflammation and AHR (Hansen G et al, J Clin Invest 105:61-70). Furthermore, the blockade of TGFβ signaling in mature T cells enhanced airway inflammation and AHR, suggesting that the regulation of T cells via TGFβ reduces inflammatory responses in the lungs (Nakao A et al, J Exp Med 192:151-158). In contrast to these observations supporting an anti-inflammatory role for TGFβ1, the secretion of TGFβ1 after an allergic disorder developed contributes to fibrosis and the irreversible changes associated with airway remodeling in chronic asthma (Aubert J. D., Thorax 49:225-232, 1994). TGFβ1 is implicated in several aspects of fibrosis, including the deposition of extracellular matrix (ECM) components such as collagens type I and III, fibronectin, vitronectin, tenascin and proteoglycans (Massague J, Annu. Rev. Cell Biol. 6:597-641, 1990). In addition, it decreases synthesis of enzymes that degrade the ECM, such as collagenase and stromelysin, and increases synthesis of inhibitors of these enzymes, including tissue inhibitor of metalloprotienase-1 (TIMP-1) and plasminogen activator inhibitor type-1 (PAI-1) (Massague J, Annu. Rev. Cell Biol. 6:597-641, 1990). TGFβ1 mRNA levels in eosinophils are increased in patients with severe asthma as compared to mild asthma (Minshall et al, Am J Respir Cell Mol Biol 17:326-333, 1997; Ohno I et al, Am J Respir Cell Mol Biol 15: 404-409, 1996). Also in most, but not all studies, TGFβ1 expression correlates with basement membrane thickness and fibroblast number and/or disease severity. TGFβ1 is therefore a promising candidate gene for asthma. A PCT patent application WO0208468 of Moscowitz (2001) titled "Diagnostic polymorphisms for the TGF-beta1 promoter" identified two single nucleotide polymorphisms (SNPs) at positions 216 and 563 on the TGF-p1 Promoter and have shown association with various diseases including cancer, diabetes, COPD, coronary heart disease, hypertension, asthma, anxiety etc.

Various studies indicate that repeats are involved in gene regulation. In addition to the above mentioned SNPs, putative repetitive sequences in and around the TGFβ1 gene were identified by us using the RepeatMasker™ Software. A CT/CA repeat 24.9 kb upstream of the TGFβ1 gene was validated for distribution in our study population (Nagpal et al, J Allergy Clin Immunol. 115(3):527-33, 2005). It is biologically relevant to study repetitive sequences in and around the genes as it is a known fact that repetitive sequences found hundreds of bases away from the coding sequence may be involved in the regulation of gene expression through long-range interactions with the basic promoter and the trans-acting proteins. A change in repeat number can alter the nucleosomal positioning thereby altering transcriptional activity. Also, variable repeats can form secondary structures, which can augment or interfere with the gene expression (Hefferon et al, PNAS 101(10):3504-3509, 2004).

Thus, modulation of the levels of TGFβ1 by transcriptional and translational mechanisms may be responsible for the wide array of actions mediated by this cytokine. In light of the above evidence, it appears that TGFβ1 could be an important genetic locus affecting the predisposition of an individual towards various immunological disorders, including atopic asthma, COPD, hypertension, anxiety, arthritis, etc.

Studies carried out in different populations have identified various polymorphisms in the regulatory and coding regions of this gene. Particularly, the C to T transition at −509 position in the promoter region induces a YY1 consensus-binding site within a negative regulatory region of TGFβ1 transcription (Shrivastava et al, Nucleic Acids Research 24:5151-5155, 1994). This substitution has previously been associated with elevated IgE levels (Hobbs K et al, Am J Respir Crit Care Med 158:1958-1962, 1998) and TGFβ1 levels (Grainger et al, Hum Mol Genet 8:93-97, 1999).

In another study, this polymorphism was associated with asthma severity, with a greater proportion of individuals having the TT genotype in the severe asthmatics group as compared to the mild and control group (Pulleyn L J et al, Hum Genet 109(6):623-627; 2001). In accordance with the study in the Caucasian population (Pulleyn et al, Hum Genet 109:623-627, 2001), we have found the association of the −509C/T polymorphism with asthma and serum IgE. In our study population, the CC genotype was over-represented in the control group and on being changed to CT, a significant increase in risk was observed. We also observed that the individuals with CC genotype had the lowest TGFβ1 levels in their serum followed by CT while the TT homozygotes had the highest levels (Nagpal et al, J Allergy Clin Immunol. 115(3):527-33, 2005). Our observations support the study conducted by Silverman et al. (Am J Respir Crit Care Med 169(2):214-219, 2004). Also, the −509C/T polymorphism plays a greater role in asthma as seen in a recent study by Silverman et al (Am J Respir Crit Care Med 169(2):214-219, 2004), which showed that the C to T transition at position −509 augments Yin-Yang1 (YY1) transcription factor binding and enhances basal promoter function for TGFβ1 gene; the T allele thus being associated with higher levels of TGFβ1 transcript.

A similar study in the Czech population however showed no association with asthma (Buckova I et al, Allergy Net 1236-1237). In the same study, four other polymorphisms, −988C/A, −800G/A, 869T/C and 915G/C, were assessed for association with asthma but no significant association was found with the asthmatic phenotype.

These studies suggest that there is a component of ethnic variation that is involved which depends on the particular population under study. In the present study, the CC genotype at −509 locus is present at a higher frequency in the controls, thereby being protective in nature. The TT genotype however is present at similar frequencies in the case and control groups. Also, in initial genotyping of TGFβ1 polymorphisms, two SNPs (−988 C/A and 788 C/T), reported to be polymorphic in populations of other ethnicities were found to be non-polymorphic in the Indian population (N=200). The difference in results obtained in our population could be explained by ethnic differences that exist between our population and the other populations studied. Also, the sampling strategies used in the studies are different. The sampling strategy used by the applicants is a case control study although they have recruited individuals with a familial history of asthma and atopy.

The two SNPs assessed in the study population lie within the promoter region of the gene. Polymorphisms in the promoter region of the gene can lead to abnormal transcriptional regulation. It is known that the C to T transition at the −509 position creates a Yin-Yang1 (YY1) transcription factor binding site, which possibly augments the basal promoter function for the TGFβ1 gene (Silverman et al, Am J Respir Crit Care Med 169(2):214-219, 2004). Also the polymorphism at −800 representing a G to A transition lies in a CREB transcription factor binding site (Grainger et al, Hum Mol Genet 8:93-97, 1999).

The present invention for the first time report a novel polymorphism wherein a CT/CA repeat 24.9 kb upstream of the TGFβ1 gene has been identified. This polymorphism along with two known polymorphisms viz. G/A at −800 and C/T at −509 position in the promoter of TGFβ1 gene, has been shown to be associated with susceptibility for immunological disorders, asthma in particular. This is the first time demonstration of the association of a combination of three polymorphisms in the TGFβ1 gene with immunological disorders, particularly asthma.

Here the applicants have for the first time provided novel gene variants and haplotypes useful for prediction of immunological disorders, particularly asthma.

The invention also provides novel primers for detection of novel polymorphism, a CT/CA repeat 24.9 kb upstream of the TGFβ1 gene.

To summarize, this is the first study in any population, identifying novel protective and risk haplotypes of the TGFβ1 gene (especially in comparison to that undertaken by Silverman et al, Am J Respir Crit Care Med, 169, 214-9, 2004). These haplotypic combinations have further been functionally validated. In addition to supporting the already known association of −509C/T polymorphism with the TGFβ1 levels, it is reported here the association of the $(CT)_n(CA)_m$ repeat alleles with the TGFβ1 levels. In contrast to earlier observations, where TGFβ1 was primarily implicated to mediate anti-inflammatory actions; in the present study, low TGFβ1 levels associated with protective genotypes as well as haplotypes point towards the pro-inflammatory role of this cytokine. During the development of an allergic reaction, TGFβ1 is a negative regulator of inflammation, but in the case of chronic asthma (as in the patient population studied by us), where the inflammatory conditions have already established, TGFβ1 exacerbates lung deterioration, thus having a pro-inflammatory role (Nagpal et al, J Allergy Clin Immunol 115: 527-533, 2005). Thus, both genetic and biochemical evidence indicates that TGFβ1 is a potential candidate gene for disease pathogenesis and/or susceptibility to asthma. To elucidate its role in asthma genetics, in the present study a case-control study in 2 independent cohorts namely Cohort A and Cohort B of patients with asthma and controls was performed. Here, we have genotyped a novel repeat (accession number BV209662) and 2 SNPs, −800G/A and −509C/T, encompassing a region of 24.7 kb, and have analyzed the association of these polymorphisms independently and at the level of haplotype with asthma and also with serum TGF-b1 levels.

OBJECTS OF THE INVENTION

The main object of the present invention is to provide novel protective and risk haplotypes of the Transforming Growth Factor Beta 1 (TGFβ1) for prediction of susceptibility to immunological disorders.

Another object of the invention is to provide a method for studying association of TGFβ1 haplotypic and allelic variants with immunological disorders.

Still another object of the invention is to provide a method for screening disease prone individuals in a given population by screening for the TGFβ1 gene variants Yet another object is to provide specific primers for detection of single nucleotide polymorphisms and specific repetitive sequences in the TGFβ1 gene.

Another object is to provide the haplotypes generated by the allelic variants of the TGFβ1 gene in the general (control) population.

Yet another object of the invention is to provide a method for predicting an individual's risk towards developing immunological disorders, specifically atopic asthma, by studying the haplotype pattern.

Still another object of the invention is to provide a method for predicting an individual's tolerance to immunological disorders, specifically atopic asthma, by analyzing the haplotype pattern.

SUMMARY OF THE PRESENT INVENTION

Asthma is a chronic lung disorder characterized by inflammation as a result of complex interactions between cells, their mediators and tissues in the airways. Various genetic and environmental factors are known to affect the disease process. Of the genetic factors, human Transforming Growth Factor Beta1 (TGFβ1) is an important candidate gene for causation of susceptibility and/or pathogenesis. TGFβ1 plays a dual role. On one hand, where it suppresses inflammation and decreases airway hyper reactivity in lungs, it also has a pro-inflammatory role where it is one of the mediators involved in subepithelial fibrosis, which is a fundamental feature of the remodeled airway in chronic asthmatics. The present invention is related to the haplotypes of human Transforming Growth Factor Beta1 (TGFβ1) and prediction of susceptibility for immunological disorders. The present invention also relates to allelic variants of the human Transforming Growth Factor Beta1 (TGFβ1) gene. The said invention also provides primers and methods suitable for the detection of these haplotypes and allelic variants for the prediction of an individual's disease susceptibility, and/or the genetic analysis of the TGFβ1 gene for immunological disorders. Specifically, the invention provides a method for detection of predisposition to atopic disorders such as asthma and various other immunological disorders such as, fibrosis, tuberculosis, sarcoidosis, cancer, COPD, hypertension, arthritis, heart diseases, atherosclerosis, etc.

DETAILED DESCRIPTION

TGFβ1 has been found to be a promising candidate gene for finding association with immunological disorders, particularly asthma as several reports have detailed occurrence of polymorphisms in this gene.

A PCT patent application WO0208468 of Moscowitz (2001), titled "Diagnostic polymorphisms for the TGF-beta1 promoter" identified two single nucleotide polymorphisms (SNPs) at positions 216 and 563 on the TGF-p1 Promoter and have shown association with various diseases including cancer, diabetes, COPD, cholecystectomy, degenerative joint disease, seizure disorders, arthritis, coronary heart disease, hypertension, asthma, anxiety etc.

Studies carried out in different populations have identified various polymorphisms in the regulatory and coding regions of this gene. Particularly, the C to T transition at −509 positions in the promoter region induces a YY1 consensus-binding site within a negative regulatory region of TGFβ1 transcription (Shrivastava et al, Nucleic Acids Research 24:5151-5155, 1994; Silverman et al, Am J. Resp. Crtic Care Med., 169: 214-219, 2004). This substitution has previously been associated with elevated IgE levels (Hobbs K et al, Am J Respir Crit Care Med 158:1958-1962, 1998) and TGFβ1 levels (Grainger et al, Hum Mol Genet 8:93-97, 1999). In another study, this polymorphism was associated with asthma severity, with a greater proportion of individuals having the TT genotype in the severe asthmatics group as compared to the mild and control group (Pulleyn L J et al, Hum Genet 109(6):623-627; 2001). In the same study, four other polymorphisms, −988C/A, −800G/A, 869T/C and 915G/C, were assessed for association with asthma but no significant association was found with the asthmatic phenotype. A similar study in the Czech population however showed no association with asthma (Buckova I et al, Allergy Net 1236-1237). These studies suggest that there is a component of ethnic variation that is involved which depends on the particular population under study.

The present application provides a dinucleotide polymorphic repeat at nucleotide 52106 to nucleotide 52151, in the clone AC011462, which is 24,927 bp upstream of the TGFβ1 gene. (GenBank contig accession no. AC011462). The first polymorphic site (CT/CA), as shown in FIG. 1, is 25,769 bp upstream of the ATG site (Genbank Accession No. AC011462, nucleotide 52106 to nucleotide 52151; Genbank Accession No. BV209662). The second polymorphic site (S1) is situated 800 bp upstream of the human TGFβ1 gene and represents a G to A transition (Genbank Accession No. AC011462, nucleotide 76280). The third polymorphic site S2 is a C to T transition, situated 509 bases upstream of the TGFβ1 gene (Genbank Accession No. AC011462, nucleotide 76571).

The present results of the present study provide very unique results as compared to the prior arts. In addition to identifying, genotyping and establishing a positive association of the novel CT/CA repeat with asthma, the inventors have found an association of the known −800G/A and −509C/T polymorphisms in the Indian population. In contrast to the study by Pulleyn et al, in the present study, the TT genotype at the −509 locus has a similar distribution in the patient and control group whereas the CC genotype is present at a higher frequency in the controls, thus having a protective effect in the Indian population. The association of TGFβ1 variants with asthma are not based only on the ethnic differences observed in the present population and the Caucasian populations, but found generally in any population of the world.

The present invention has identified the novel genetic variants, which exist in any type of population in the world irrespective of its origin, community, colour, geographical location or ethnicity. The inventors have compared allele frequencies in CT/CA repeat polymorphism 24.9 kb upstream of promoter and −800 G/A, −509 C/T SNPs in the promoter and the haplotypes generated using the three loci, in a population. Also, the sampling strategies used in the present studies are different. The present study is a case control study although the inventors have recruited individuals with a familial history of asthma and atopy. Further, the invention clearly defines that the variants identified would be useful for any kind of population of any geographical origin.

Earlier studies indicate that dinucleotide repeats located far upstream of the promoter are involved in gene regulation (Texerdau et al, Thorax 59:156-158, 2004; Holbert et al, Proc Natl Acad Sci USA: 98(4):1811-18166, 2001; Chakraborty et al, Biochem Biophys Res Commun 252:716-722, 1998). For example, a far upstream $(CA)_n$ repeat (allele 25) was found to repress Ha-ras gene activity (Chakraborty et al, Biochem Biophys Res Commun 252:716-722, 1998). In our study, the alleles of the $(CT)_n(CA)_m$ locus showed a significant difference in distribution pattern amongst the patient and the control groups Table 1: Interestingly, the different alleles were found to be associated with different levels of TGFβ1 Table 5. However, the functional role of these repeats is yet to be established.

To further the understanding of the contributions of this gene towards asthma, we constructed three-locus haplotypes using PHASE (Stephens et al, Am J Hum Genet 68:978-989, 2001). The overall distribution of the different haplotypic combinations was significantly different in the patients and the controls. In addition, we identified two major haplotypes, namely 22_G_C and 24_G_C as protective haplotypes for asthma. In contrast, the haplotypes 21_G_C and 23_G_T increase the susceptibility of the patient to develop this disorder, marking them as the major risk haplotypes. As already validated for the $(CT)_n(CA)_m$ and −509 locus individually, the protective haplotypes were associated with lower serum TGFβ1 levels and vice-versa. Particularly, the individuals homozygous for the 22_G_C haplotype have the lowest levels of TGFβ1, followed by heterozygous individuals while the ones lacking this haplotype have the highest levels of TGFβ1 in their sera Table 5. This dose dependency is also reflected in the individuals with 23_G_T, wherein individuals homozygous for this haplotype have the highest levels of TGFβ1 in their sera. Thus, the polymorphisms constituting the three-locus haplotypes may be controlling TGFβ1 levels directly or may be present in linkage disequilibrium with another true functional polymorphism(s) within and/or around the gene. Although, the number of individuals homozygous for either the 22_G_C or the 23_G_T haplotypes were few (n=5 and n=3 respectively), the difference in TGFβ1 levels with each haplotype was highly significant (p=0.0019 in case of 22_G_C and p=0.01 for the 23_G_T haplotype). Also, appreciable numbers of individuals, heterozygous for either haplotype, have corroborated this observation further. However, to gain an insight into tissue specific expression of TGFβ1, these results have to be further validated using BAL fluid/lung biopsy samples.

Since asthma is a complex disorder, we conducted a case-control study here that could provide better directions on promising loci (Sharma et al, Clin Genet. 66(5):417-25, 2004). These leads can be further tested using a well-controlled family-based study. Indeed, we have established the genetic homogeneity between the two groups by genotyping multiple loci to eliminate the errors due to stratification or an inherent statistical bias (Sharma et al, Clin Genet. 66(5):417-25, 2004). Moreover, the additional unlinked regions used as controls (Zak et al, Drug Discov Today 6:1111-1115, 2001) and validation of our results in another independent cohort could only add more confidence to our results.

Therefore the present study is of first kind wherein in any population, novel protective and risk haplotypes of the TGFβ1 gene have been identified. Further, the present study also shows the functionally validity of these haplotypes and the identified genetic variants. In addition to support the already known association of −509C/T polymorphism with the TGFβ1 levels, the present invention reports the association of the $(CT)_n(CA)_m$ repeat alleles with the TGFβ1 levels. In contrast to earlier observations, where TGFβ1 was primarily implicated to mediate anti-inflammatory actions; in present study, low TGFβ1 levels associated with protective genotypes as well as haplotypes point towards the pro-inflammatory role of this cytokine. During the development of an allergic reaction, TGFβ1 is a negative regulator of inflammation, but in the case of chronic asthma (as in the patient population studied in the present study), where the inflammatory conditions have already established, TGFβ1 exacerbates lung deterioration, thus having a pro-inflammatory role.

Accordingly, the present invention provides novel haplotypes of human Transforming Growth Factor Beta1 (TGFβ1) gene having SEQ ID Nos. 1, 2 and 3 and useful for prediction of susceptibility (low or high risk) of an individual to immunological disorders, particularly asthma.

In an embodiment the invention, novel haplotypes of human Transforming Growth Factor Beta1 (TGFβ1) gene having SEQ ID Nos. 1, 2 and 3 useful for prediction of susceptibility (low or high risk) of an individual to immunological disorders, particularly asthma.

Another embodiment the invention, the said haplotypes are useful for predicting and detecting humans susceptible to the immunological disorders selected from group comprising of asthma, and various other immunological disorders such as, fibrosis, tuberculosis, sarcoidosis, cancer, COPD, hypertension, arthritis, heart diseases, atherosclerosis, etc. wherein TGFβ1 plays an important role.

Yet another embodiment the invention, the said immunological disorder selected is asthma.

Still another embodiment of the invention, the said haplotype is pharmacogenetic marker for predicting and detecting humans susceptible to the immunological disorders selected from group comprising of asthma, and various other immunological disorders such as, fibrosis, tuberculosis, sarcoidosis, cancer, COPD, hypertension, arthritis, heart diseases, atherosclerosis, etc. wherein TGFβ1 plays an important role.

An embodiment the invention, the haplotype is pharmacogenetic marker for predicting and detecting humans susceptible to asthma.

Another embodiment of the invention relates to a method of detecting novel haplotypes of human Transforming Growth Factor Beta1 (TGFβ1) gene having SEQ ID Nos. 1, 2, and 3 and useful for prediction of susceptibility (low or high risk) of an individual to immunological disorders. The said method comprising the steps of:

(i) designing primers having sequence ID no. 4 & 5.

(ii) synthesizing primers having SEQ ID Nos. 4, 5, 6, 7, 8 and 9.

(iii) amplifying the genomic DNA using primers of SEQ ID Nos. 4, 5, 6, 7, 8 and 9 wherein primers of SEQ ID Nos 4, 6 and 8 are forward primers and primers of SEQ ID Nos. 5, 7 and 9 are reverse primers.

(iv) isolating and identifying the DNA stretch of SEQ ID No. 1 using novel primer combinations of SEQ ID Nos. 4 and 5, (v) isolating and identifying the DNA stretch of SEQ ID No. 2 using primer combinations of SEQ ID Nos. 6 and 7, (vi) isolating and identifying the DNA stretch of SEQ ID No. 3 using primer combinations of SEQ ID Nos. 8 and 9, (vii) sequencing the isolated and identified SEQ ID Nos. 1, 2 and 3 obtained in steps (iv, v and vi)

Another embodiment to the invention, SEQ ID #1 is associated with CT/CA, SEQ ID #2 is associated with S1 and SEQ ID #3 is associated with S2 locus of the TGFβ1 gene.

Still another aspect of the invention is to provide a method of preparing novel pharmacogenetic markers for detecting and predicting predisposition to immunological disorders of TGFβ1 gene in a subject, said method comprises of:

(i) designing primers having sequence ID no. 4 & 5.

(ii) synthesizing primers having SEQ ID Nos. 4, 5, 6, 7, 8 and 9.

(iii) amplifying the genomic DNA using primers of SEQ ID Nos. 4, 5, 6, 7, 8 and 9 wherein primers of SEQ ID Nos. 4, 6 and 8 are forward primers and primers of SEQ ID Nos. 5, 7 and 9 are reverse primers.

(iv) isolating and identifying the DNA stretch of SEQ ID No. 1 using novel primer combinations of SEQ ID Nos. 4 and 5, (v) isolating and identifying the DNA stretch of SEQ ID No. 2 using primer combinations of SEQ ID Nos. 6 and 7, (vi) isolating and identifying the DNA stretch of SEQ ID No. 3 using primer combinations of SEQ ID Nos. 8 and 9, (vii) sequencing the isolated and identified SEQ ID Nos. 1, 2 and 3 obtained in steps (iv, v and vi)

(viii) validating and identifying the specific TGFβ1 gene variants computationally by comparison with the known wild type TGFβ1 gene sequences, Another embodiment of the present invention the subject is a human.

Yet another aspect of the invention provides a diagnostic kit for detecting and predicting predisposition to immunological disorders by screening for TGFβ1 gene haplotypes in a subject, said kit comprising of:

(i) Primers corresponding to SEQ ID Nos. 4, 5, 6, 7, 8 and 9.

(ii) Standard Human DNA for control experiment.

(iii) Reagents and buffers for carrying out a polymerase chain reaction and sample extraction.

In yet another embodiment of the invention, SEQ ID #1 is associated with CT/CA, SEQ ID #2 is associated with S1 and SEQ ID #3 is associated with S2 locus of the TGFβ1 gene.

In yet another embodiment of the invention, the said haplotypes of the diagnostic kit are useful for predicting and detecting humans susceptible to immunological disorders selected from group comprising of asthma, and various other immunological disorders such as, fibrosis, tuberculosis, sarcoidosis, cancer, COPD, hypertension, arthritis, heart diseases, atherosclerosis, etc. wherein TGFβ1 plays an important role.

In yet another embodiment of the invention, the said haplotypes of the diagnostic kit useful for predicting and detecting humans susceptible to asthma.

One more embodiment of the present invention provides pharmacogenetic markers for detecting and predicting predisposition to immunological disorders by screening for TGFβ1 gene haplotypes in a subject, said kit comprising of:

(i) Primers corresponding to SEQ ID Nos. 4, 5, 6, 7, 8 and 9.

(ii) Standard Human DNA for control experiment, (iii) Reagents and buffers for carrying out a polymerase chain reaction and sample extraction.

I. Detailed Methodology

Isolation of Genomic DNA from Peripheral Blood Leukocytes of the Atopic Asthmatic Patients and the Normal Control Individuals Genomic DNA was isolated from the peripheral blood of the patients and control individuals using a modified salting out procedure (Nagarkatti R et al., 2002). Briefly, 10 ml blood was obtained from patients and unrelated control individuals using ACD Vaccutainers (BD Biosciences, San Jose, Calif., USA). Equal volume of ice cold C1 buffer (4×) was added and then 30 ml of ice cold sterile water was added to cause cell membrane lysis (Promega Genomic DNA Isolation Handbook). Following this, the nuclei were pelleted at 1300×g for 15 min at 4° C. The pellet was washed again with 1× C1 buffer. 12 ml of nuclear lysis buffer was added with 0.8 ml of 10% SDS. 50 μl of a 20 μg/μl solution of proteinase-K was added and the pellet resuspended by brief vortexing. After incubation at 65° C. for 2-3 hrs, the proteinaceous material was precipitated with the addition of 4 ml of 6M NaCl. After centrifugation for 15 min at 2500 rpm, the supernatant was transferred to another tube and two volumes of absolute ethanol (at room temperature) was used to precipitate the DNA (Miller et al., 1988). The precipitated DNA was then washed with 70% ethanol twice, air-dried, and dissolved in TE buffer. Appropriate dilutions (1:100, in T.E buffer) were used to determine the OD at 260 nm and 280 nm. DNA quality was assessed using the 260 nm/280 nm ratio. The stock solution of the DNA was diluted to 50 ng/μl and used for PCR amplification and genotyping experiments. The stock DNA solution was stored at −20° C.

Identification of Putative Repeats in and Around the TGFβ1 Gene Using RepeatMasker™ Software A novel CT/CA repeat was identified to be present 24.9 kb upstream of the TGFβ1 gene in the study population using RepeatMasker™ Software Designing and Synthesis of Two New Oligonucleotide Primers (Sequence ID #4, 5) for PCR Amplification of 363 bp Region, 24.9 kb Upstream of TGFβ1 Gene Containing CT/CA Polymorphism PCR amplification of genomic. DNA samples isolated from peripheral blood leukocytes of the atopic asthmatic patients and normal control individuals using the primers of Table 1. For the CT/CA locus, PCR was carried out in a total volume of 15 μl containing 25 ng of genomic DNA, 4 pmol each of a 6-FAM-labeled forward primer and a non-labeled reverse primer, 1.5 Mm MgCl$_2$, 0.25 mM of each dNTP, 0.03 U/μl of Taq DNA polymerase (Bangalore Genie, India) and the buffer recommended by the supplier. After PCR, 1 μl of the PCR product was loaded with and internal size standard (ROX labeled) on ABI Prism 3100 Genetic Analyzer (Applied Biosystems). Fragment lengths were determined using the GeneScan Analysis Software version 3.7 (Applied Biosystems). The number of repeat for each loci was determined by sequencing PCR fragments of individuals (N=5) being

PCR Amplification of 388 and 418 bp Stretches of the Promoter Region of TGFβ1 Gene Containing −800 G/A and −509 C/T Polymorphisms Respectively PCR amplification of genomic DNA samples isolated from peripheral blood leukocytes of the atopic asthmatic patients and normal control individuals using the primers of Table 1. For the −800 G/A polymorphism, PCR was carried out in a total volume of 25 μl containing 50 ng of genomic DNA, 1.25 pmol each of forward and reverse primers (sequence ID #6, 7), 1.5 mM $MgCl_2$, 0.25 mM of each dNTP, 4% DMSO, 0.03 U/μl of Taq DNA polymerase (Bangalore Genie, India) and the buffer recommended by the supplier.

For the −509 C/T polymorphism, PCR was carried out in a total volume of 10 μl containing 25 ng of genomic DNA, 2.5 pmol each of forward and reverse primers (sequence ID #8, 9), 1.5 mM $MgCl_2$, 0.25 mM of each dNTP, and 0.03 U/μl of Taq DNA polymerase (Bangalore Genie, India) and the buffer recommended by the supplier.

Direct Sequencing of the Purified PCR Products

Direct sequencing of the purified PCR products using dye terminator chemistry was carried out on an ABI Prism 3100 automated DNA sequencer. Sequencing was carried out using specific primers on an ABI 3100 capillary sequencer (Applied Biosystems, Foster City, Calif., USA) for a minimum of 20 atopic asthmatic and 20 control individuals. Nested primers were used for sequencing the entire PCR amplicons. PCR product was gel purified for sequencing. Briefly, sequencing primers, diluted to 1 pmol per μl, and 75-150 ng/μl PCR product were added to 5 μl reaction mix, and volume made up to 10 μl with autoclaved MilliQ water as per the Big Dye Terminator kit instructions (Applied Biosystems, Foster City, Calif., USA). PCR was set up with the following conditions: 96° C. for 5 seconds, 55° C. for 30 seconds and 60° C. for 4 minutes. Sequencing reactions were purified with 70% ethanol washes to remove unincorporated primers and fluorescent ddNTPs. Briefly, 26 μl autoclaved MilliQ water was added to the sequencing reaction. Sixty-four microliters of chilled 100% ethanol was added to the tubes and vortexed. The tubes were centrifuged at 16,000 g for 20 minutes at room temperature. Washes were performed with 70% ethanol by centrifugation at 16,000 g for 5 minutes. The pellets were air dried and resuspended in 10 μl of 100% Hi-Dye formamide. The tubes were incubated at 94° C. for 5 minutes and placed in the 3100 Automated Sequencer. Sequence analysis was carried out using Sequence Navigator (ver 2.1, Applied Biosystems, Foster City, Calif., USA) and DNAStar (ver 1.1, DNASTAR) software. Homozygous and heterozygous alleles were scored manually.

Validation of −800 G/A Polymorphism

The −800 G/A polymorphisms were studied using SNaPshot ddNTP Primer Extension Kit (Applied Biosystems, Foster City, USA). SnaPshot PCR was carried out using 50 ng purified PCR template, 1 pmol primer, ABI ready reaction mix and 1× dilution buffer (as supplied by the manufacturer). PCR was set up with the following conditions: 96° C. for 10 seconds, 50° C. for 5 seconds and 60° C. for 30 seconds for a total of 35 cycles. To clean up the primer extension reaction, 1 U of calf intestinal phosphatase (CIP) diluted in 10× NEB3 (New England Biolabs), was added to the reaction mixture and the mixture was incubated at 37° C. for 1 hour, followed by an incubation for 15 minutes at 72° C. for enzyme inactivation. These samples were subsequently electrophoresed using the ABI Prism 3100 Genetic Analyzer as per the manufacturer's instructions. The results were analyzed using the program ABI Prism GeneScan™ and Genotyper™ (Applied Biosystems, Foster City, USA).

Calculating and Estimating the Frequency of Single Nucleotide Polymorphisms, −800G/A and −509C/T and that of Repeat Polymorphism CT/CA Kolmogorov-Smirnov test has been used to test for allelic association with disease for CT/CA locus (Table 2). Odds ratios were calculated and Chi-square test for association with phenotype, was carried out. The repeats have been denoted with the allele size (19, 20 etc for CT/CA), the genotypes with (19/20 for CT/CA), whereas the SNPs are designated as S1 and S2.

Estimating the frequencies of haplotypes generated using the above mentioned three loci in the normal individuals and atopic asthmatic patients for finding association between these haplotypes and the disease:

Novel Haplotypes have been generated using the PHASE program for the patient and control groups (Stephens M, Am J Hum Genet. November 73:1162-9, 2003). Default parameters were used to generate the haplotypes. No missing values were allowed (http://archimedes.well.ox.ac.uk/pise/PHASE-simple.html, PHASE Ver. 2.0.2). Odds ratios were calculated and Chi-square test for association with phenotype, was carried out. The haplotypes are designated as CT/CA_S1_S2 or 19_G_C, 22_G_C etc.

So the matter in which the above mentioned features, advantages and the objects of the invention, as well as others which will become clear, are attained and can be understood in detail. These drawings form a part of the specification. It is to be noted, however, that the appended drawings illustrate preferred embodiments of the invention and therefore not to be considered limiting in their scope.

BRIEF DESCRIPTION OF THE ACCOMPANYING DRAWINGS AND TABLES

FIG. 1: The gene structure and polymorphisms investigated in the TGFβ1 gene. The positions marked in bold were found polymorphic in the Indian population FIG. 2: The frequency distribution of the haplotypes of the TGFβ1 gene in patients and unrelated controls in cohorts A and B, respectively. The haplotypes were plotted on the X-axis and their respective relative frequencies (%) on the Y-axis.

Table 1: Primer details for the PCR.

Table 2: Alleles frequencies of the CT/CA polymorphism upstream of the TGFβ1.

Table 3: Distribution of Allele and genotype frequencies for −800 G/A and −509 C/T polymorphism.

Table 4: Multiple logistics regression analysis of the TGFβ1 polymorphisms for risk of asthma.

Table 5: Serum TGFβ1 levels in context of alleles, genotypes and haplotypes
Table 6: Profile and characterstics of study populations Association of the CT/CA Repeat Locus with Atopic Disorders such as Asthma To demonstrate the association of the CT/CA repeat locus with atopic disorders such as asthma, Kolmogorov-Smirnov test was performed (Nagarkatti et al., 2000; Carriere and Kochar 2000, Mukawa et. al., 1989). The Kolmogorov-Smirnov Test is a non-parametric test, which gives the likelihood of two ordered categorizations coming from different orderings or the same ordering. The Kolmogorov-Smirnov test (KS-test) tries to determine if two datasets differ significantly. The KS-test has the advantage of being more powerful than the chi-square test in many situations. We identified a novel $(CT)_n(CA)_m$ repeat polymorphism, 24.9 kb upstream of the TGFβ1 gene (FIG. 1) and used it for genotyping patients and controls in two independent cohorts. A total of seven alleles were obtained for cohort A (heterozygosity index=0.728) and six alleles for cohort B (heterozygosity index=0.730) (FIG. 2). A highly significant difference was obtained in the allele count in the patients and the controls (KS $\chi^2$=34.22, df=6, p=0.00001 in cohort A and KS $\chi^2$=11.29, df=5, p=0.003 in cohort B). The distribution was statistically significant after Bonferroni correction ($^a\alpha$=0.007, $^b\alpha$=0.008) in both the cohorts. One-way ANOVA showed an association between the alleles at this locus and log total serum IgE levels in the patients {F-ratio (F)=2.76, df=6, p=0.012}. Tukey-Kramer HSD (Honestly Significant Difference) showed significant difference between mean log IgE levels for the pair of alleles: 22 and 23. However, none of the genotypes at the CT/CA locus was associated with log total serum IgE levels (F=1.34, df=16, p=0.17).

Demonstration of Association of −800 G/A Polymorphism with Asthma

To demonstrate the association of −800 G/A polymorphism, $\chi^2$ test was performed. Of the three genotypes, AA, GA, GG; AA was the rare genotype with only one individual in the control group having AA at −800 locus. Excluding AA genotype from the analysis, a significant difference in the distribution of the genotypes was observed between the patient and the control groups ($\chi^2$=4.89, df=1, p=0.026) (Table 3).

To demonstrate the association of −509 C/T polymorphism, $\chi^2$ test was performed. The pattern of distribution of the three genotypes, CC, CT, TT was significantly different in the two groups studied ($\chi^2$=10.03, df=1, p=0.006). The CC genotype was predominant in the controls as compared to the patient group {OR=0.51, 99% C.I. (0.30, 0.89)} (Table 3).

Logistic Regression Analysis for the Polymorphisms Investigated

Using multiple logistic regression analyses, we confirmed the association between the $(CT)_n(CA)_m$, −800G/A and −509C/T polymorphisms with asthma and it was found not to be influenced by sex and age (Table 4).

Generation of Haplotypes

We then used the PHASE program to generate haplotypes for the patient and control groups. The program PHASE implements a new statistical method for reconstructing haplotypes from population genotype data. Experiments with the software on both real and simulated data indicate that it can provide an improvement on the EM algorithm for reconstructing haplotypes. It allows for missing genotype data and also can handle more than one locus irrespective of the polymorphism, for example SNPs and repeats can be analyzed simultaneously. Based on the output from the software the probability values of the haplotypes are also predicted and can be utilized to differentiate more confident haplotypes. The PHASE software is suitable for genetic distances of 100 cM or less. The probability values for the chromosomes with uncertain phase ranged form 0.51 to 0.65 for both the groups; these chromosomes accounted for only 2.07% of the control and 2.60% of the patient chromosomes. The haplotypes are shown in FIG. 2. The haplotypes 21_G_C and 23_G_T were the most frequent in the patient population. The odds of patients rather than controls having 21_G_C was 2.45 with 99% CI=(1.58, 3.94) [Likelihood $\chi^2$=27.92, df=1, p=0.00001] and 1.38 with 95% CI=(1.01, 1.87) [Likelihood $\chi^2$=4.21, df=1, p=0.04] for cohort A and B respectively. Similarly, the odds of patients rather than controls having 23_G_T was 2.64 with 99% CI=(1.51, 4.59) [Likelihood $\chi^2$=21.77, df=1, p=0.00001] and 3.55 with 99% CI=(2.00, 6.29) [Likelihood $\chi^2$=37.22, df=1, p=0.00001] for cohort A and cohort B respectively. These results suggest that 21_G_C (in cohort A) and 23_G_T (in both cohorts) are risk/susceptibility haplotypes and are positively associated with asthma. On the other hand, the haplotypes 22_G_C and 24_G_C were the most frequent in the control population. The odds (OR) of patients rather than controls having 22_G_C was 0.18 with 99% CI=(0.10, 0.31) [Likelihood $\chi^2$=35.32, df=1, p=0.00001] and 0.33 with 99% CI=(0.20, 0.54) [Likelihood $\chi^2$=72.28, df=1, p=0.00001] for cohort A and B respectively. Similarly, the odds of patients rather than controls having 24_G_C was 0.48 with 95% CI=(0.24, 0.98) [Likelihood $X^2$=4.28, df=1, p=0.038] and 0.28 with 99% CI=(0.12, 0.68) [Likelihood $\chi^2$=16.01, df=1, p=0.00001] for cohort A and cohort B respectively. These results suggest that 22_G_C (in both cohorts) and 24_G_C (in cohort B) are protective haplotypes and are negatively associated with asthma.

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

Many of the methods described below require amplification of DNA from target samples. This can be accomplished by e.g., PCR. See generally PCR Technology: Principles and Applications for DNA Amplification (ed. H. A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967 (1991) and U.S. Pat. No. 4,683,202 (each of which is incorporated by reference for all purposes).

Other suitable amplification methods include the Ligase Chain Reaction (LCR) (see Barringer K J et al, Gene 89:117-22, 1990; Friedhoff P et al, Anal Biochem 215:9-16, 1993) and Nucleic Acid Based Sequence Amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

There are two distinct types of analysis depending on whether a polymorphism in question has already been characterized or not. The first type of analysis is sometimes referred to as de novo characterization. This analysis compares target sequences in different individuals to identify points of variation, i.e., polymorphic sites. By analyzing groups of individuals representing the greatest ethnic diversity among humans and greatest breed and species variety in plants and animals, patterns characteristic of the most common alleles/haplotypes of the locus can be identified, and the frequencies of such populations in the population determined. Additional allelic frequencies can be determined for subpopulations characterized by criteria such as geography, race, or gender. The de novo identification of the polymorphisms of the invention is described in the Examples section. The second type of analysis is determining which form(s) of a characterized polymorphism are present in individuals under test. There are a variety of suitable procedures, which are discussed in turn.

1. Repeat Detection (Size Variation Detection):

The design and use of primers flanking the sequence contain the repeat sequence or other polymorphic elements, which lead to a size difference. PCR amplification of the sequence leads to the presence of a pool of amplified products that differ by the specific repeat or polymorphism size. These size differences can then be detected using gel based, charge based methods. Usually for gel based detection one of the primers is labeled with a fluorescent compound which can then be excited and detected using a CCD camera or other methods.

2. Allele-Specific Probes:

The design and use of allele-specific probes for analyzing polymorphisms is described by e.g., Saiki et al., Nature 324, 163-166, 1986; Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals.

3. Allele-Specific Primers:

An allele-specific primer hybridizes to a site on target DNA overlapping a polymorphism and only primes amplification of an allelic form to which the primer exhibits perfect complementarity. This primer is used in conjunction with a second primer which hybridizes at a distal site. See, e.g., WO 93/22456.

4. Direct-Sequencing:

The direct analysis of the sequence of polymorphisms of the present invention can be accomplished using either the dideoxy chain termination method or the Maxam Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

5. Denaturing Gradient Gel Electrophoresis:

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W.H. Freeman and Co, New York, 1992), Chapter 7.

6. Single-Strand Conformation Polymorphism Analysis:

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766-2770, 1989. Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

III. Methods of Use

After determining polymorphic form(s) present in an individual at one or more polymorphic sites, this information can be used in a number of methods.

A. Correlation of Polymorphisms with Phenotypic Traits:

Atopic diseases are heterogeneous in nature and as such there are many sub-phenotypes and traits to which the association can be observed. The polymorphisms of the invention may contribute to the phenotype of an organism in different ways. As described above, the polymorphisms may act at various levels of cellular organization by which the disease phenotypes are observed as the end result. These polymorphisms may yield different selection advantages or disadvantages. For example, a heterozygous sickle cell mutation confers resistance to malaria, but a homozygous sickle cell mutation is usually lethal. A single polymorphism may affect more than one phenotypic trait.

Likewise, a single phenotypic trait may be affected by polymorphisms in different genes. Further, some polymorphisms predispose an individual to a distinct mutation that is causally related to a certain phenotype. Phenotypic traits include diseases that have known but hitherto unmapped genetic components. Phenotypic traits also include symptoms of, or susceptibility to, multifactorial diseases of which a component is or may be genetic, such as atopy, autoimmune diseases, inflammation, cancer, diseases of the nervous system, and infection by pathogenic microorganisms. Some examples of autoimmune diseases include systemic lupus eryhematosus, rheumatoid arthritis, diabetes, multiple sclerosis, (insulin-dependent and non-independent), and Graves disease. Some examples of cancers include cancers of the breast, bladder, colon, brain, etc. As such, phenotypic traits also include characteristics, for example, susceptibility or receptivity to particular drugs or therapeutic treatments.

To perform association analysis of the disease phenotypes and genetic markers, the presence or absence of a set of polymorphisms (i.e. a polymorphic set) is determined for a set/population of the individuals, some of whom exhibit a particular trait termed variously as case/patients/affected/diseased individuals etc, and some of which exhibit lack of the trait termed variously as control individuals/normal etc. The alleles of each polymorphism of the set are then counted to determine if the presence or absence of a particular allele or a set of alleles or a haplotype is associated with the trait of interest. Test for such associations can be performed by standard statistical methods such as a $\chi 2$ test, Kolmogrov-Smimov test, etc. Based on the values obtained for the hypothesis tested for example, if the allele X is present more in patients than in controls and if the allele X is not present more in patients than in controls, the significance value is obtained. If this value lies in a particular range then it determines the significance level of the correlations. For example, it might be found that the presence of allele A1 at polymorphic site 1 correlates with cystic fibrosis disease. As a further example, it might be found that the combined presence of allele A1 at polymorphic site 1 and allele B1 at polymorphic site 2 correlates with 10 fold-increased severity of cystic fibrosis.

Such associations can be of immediate benefit if an extremely strong correlation exists. For example, detection of cystic fibrosis polymorphism A1 and B1 in a patient may allow for rapid diagnosis and discrimination from other diseases which exhibit similar phenotypes; it can also allow for treatment if available; it can allow for screening of neonates for detection and/or for susceptibility and/or risk assessment; it can allow for selection of better and improved management methods for the disease from those which are available; it may allow for the treatment to be given if it is determined that the polymorphic site also correlates with particular therapeutic regimes and that such therapeutic drugs are more beneficial to the patient than other drugs.

B. Genetic Mapping of Phenotypic Traits:

The previous section concerns identifying correlations between phenotypic traits and polymorphisms that directly or indirectly contribute to those traits. The present section describes identification of a physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. Please see (Altshuler D et al, 1998, N Engl J Med 338:1626; Cargill M et al, 1999, Nat Genet 22:231-8; Chang C, 1988, Proc Natl Acad Sci USA 85:6856-60; Hacia J G et al, 1999, Nat Genet 22:164-7; Hirschhorn J N et al, 2000, Proc Natl Acad Sci USA 97:12164-9; Lander E S and Botstein D, 1986, Proc Natl Acad Sci USA 83:7353-7; Lander E S, 1993, Nat Genet 4:5-6; Reich D E et al, 2001, Nature 411:199-204; Sachidanandam R et al, 2001, Nature 409:928-33. Genes localized by linkage can be cloned by a process known as directional cloning.

Computer programs are available for the calculation of lod scores for differing values of theta. Other references on linkage and disease mapping use above mentioned approaches include, Kreutz R et al, 1995, Proc Natl Acad Sci USA 92:8778-82; de Gouyon B et al, 1993, Proc Natl Acad Sci USA 90:1877-81; Julier C et al, 1990, Proc Natl Acad Sci USA 87:4585-9; Oberle I et al, 1986, Proc Natl Acad Sci USA 83:1016-20; Lathrop G M et al, 1984, Proc Natl Acad Sci USA 81:3443-6; Cohen D et al, 1984, Proc Natl Acad Sci USA 81:1774-8.

IV. Modified Polypeptides and Gene Sequences

The invention further provides variant forms of nucleic acids. These variants can be used to identify the chromosomal backgrounds of individuals and depending on the particular haplotype, risk may be assessed. The promoter polymorphism may also be important in the production of variant gene constructs containing the gene of interest so as to allow heterologus expression of the gene in various human and non-human cell lines. 5'-UTR polymorphism may lead to variant expression level changes due to transcriptional or post translational modifications.

V. Kits

The invention further provides kits comprising at least one specific oligonucleotide pair. For example, the same substrate can be used as a template for allele-specific oligonucleotide probes for detecting all of the polymorphisms listed. For initial screening purposes, the CT/CA repeat polymorphism found 24.9 kb upstream of the human TGFβ1 gene could be useful as the allele 22 of this polymorphism is negatively associated, whereas the allele 23 is positively associated with asthma. For this locus, PCR was carried out in a total volume of 5 µl containing 25 ng of genomic DNA, 1.25 pmol each of a 6-FAM-labelled forward primer and a non-labeled reverse primer, 1.5 Mm MgCl2, 0.25 mM of each dNTP, 0.03 U/µl of Taq DNA polymerase (Bangalore Genie, India) and the buffer recommended by the supplier. After PCR, 1 µl of the PCR product was loaded with an internal size standard (ROX labeled) on ABI Prism 3100 Genetic Analyzer (Applied Biosystems). Fragment lengths were determined using the GeneScan Analysis Software version 3.7 (Applied Biosystems). The number of repeat for each loci was determined by sequencing PCR fragments of individuals (N=5) being homozygous for one allele. Repeat sizes were calculated using the formula n={(flanking region-allele size)/2, rounding off to 0 decimal values}. If subsequently required, genotyping at the other two loci, namely, −800 G/A and −509 C/T could also be carried out.

Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

The invention of the instant Application is illustrated by the help of following examples and should not be construed to limit the scope of the invention.

EXAMPLE 1

Patient and Healthy Volunteers

Unrelated patients were recruited from various hospitals in Northern India in cohort A (N=187) and Western India in cohort B (N=209), respectively (Table 6). Ethical approval was obtained from the review board of each hospital. Written informed consent was obtained from all individuals participating in the study. Asthma, in the recruited study population was defined by clinical history and validated later by interview questions (details of environmental factors, family history of asthma/atopy, the geographical region of origin and migration status). Patients (mean age 28.42±0.97 and 34.22 yrs±1.01 yrs for cohort A and B, respectively) were diagnosed for asthma on the basis of National Asthma Education and Prevention Program (Expert Panel Report-2) guidelines (National Asthma Education and Prevention Program, J Allergy Clin Immunol 110:S141-S219, 2002) and were examined for a self-reported history of breathlessness and wheezing. The clinical parameters are summarized in Table 6. Each patient showed airway reversibility as documented by an inhalant bronchodialator-induced improvement of more than 15% (using albuterol/salbutamol). Fifteen common environmental allergens were used for the skin prick test. Atopy was defined as having wheal reaction equal to or greater than histamine (3 mm diameter). All asthmatic subjects were positive to at least one antigen used for skin prick test (SPT). Total serum IgE levels were estimated for all individuals, except few individuals (<10%) where sera were not available, using ELISA (Nagarkatti et al, J Allergy Clin Immunol 110:410-412, 2002).

Healthy Volunteers (referred to as normal controls) (N=187 & 190 in cohort A and B, respectively) were recruited on the basis of the criteria of having no symptoms or history of allergic diseases. Individuals having a history of smoking and parasitic/helminthic infestations in the past were excluded from the study. All control individuals recruited for the study were screened negative for all the allergens used to perform SPT.

In this study, as the samples were collected from individuals on the basis of their family history, origin and migration status, the error due to stratification is presumably minimized (Table 6). Indeed, we have established the genetic homogeneity between the two groups by genotyping multiple loci, as yet unlinked to asthma or related atopic disorders ((Nagarkatti et al, J Allergy Clin Immunol 110:410-412, 2002)). Also, all individuals were age and sex matched (Table 6).

EXAMPLE 2

To demonstrate the association of the CT/CA repeat locus with atopic disorders such as asthma, Kolmogorov-Smirnov test was performed (Nagarkatti et al., 2000; Carriere and Kochar 2000, Mukawa et. al., 1989). The Kolmogorov-Smirnov Test is a non-parametric test, which gives the likelihood of two ordered categorizations coming from different orderings or the same ordering. The Kolmogrov-Smirnov test (KS-test) tries to determine if two datasets differ significantly. The KS-test has the advantage of being more powerful than the chi-square test in many situations. This analysis showed significant differences between the allele count distribution of patient and control groups [probability value $(p)=10^{-6}$]. We observed a significantly different pattern of distribution of the alleles between the two groups; alleles 21 and 23 were overrepresented in the patient group whereas alleles 22 and 24 were the major alleles in the control group (FIG. 2). When the cases and controls were compared with respect to the log total serum IgE levels, a highly significant difference was obtained (for cohort A: t-test=3.58, df=255, p<0.0004 and for cohort B: t-test=6.58, df=285, p<0.0004).

When the genetic effects of TGFβ1 polymorphisms were tested on serum IgE levels, a significant effect was observed at the level of alleles for the CT/AC repeat (p=0.0039 and p=0.0001 for cohort A and B, respectively). Tukey-Cramer HSD (Honestly Significant Difference) showed significant difference between mean log IgE levels for the pair of alleles: 22&23 and 21&23 for cohort A; 21&22, 21&24, 22&23 and 23&24 for cohort B. Similar results were obtained at the level of genotypes: p=0.0315 and p=0.0002 for cohort A and B, respectively.

EXAMPLE 3

To demonstrate the association of −800 G/A polymorphism, $\chi^2$ test was performed. Of the three genotypes, AA, GA, GG; AA was the rare genotype with only one individual in the control group having AA at −800 locus (Table 3). Excluding AA genotype from the analysis, a significant difference in the distribution of the genotypes was observed between the patient and the control groups ($\chi^2$=4.89, df=1, p=0.026).

EXAMPLE 4

To demonstrate the association of −509 C/T polymorphism, $\chi^2$ test was performed. The pattern of distribution of the three genotypes, CC, CT, TT was significantly different in the two groups studied ($\chi^2$=10.03, df=1, p=0.006) (Table 3). The CC genotype was predominant in the controls as compared to the patient group {OR=0.51, 99% C.I. (0.30, 0.89)}.

EXAMPLE 5

PHASE was used to construct haplotypes. It allows for missing genotype data and also can handle more than one locus irrespective of the polymorphism, for example SNPs and repeats can be analyzed simultaneously. Based on the output from the software the probability values of the haplotypes are also predicted and can be utilized to differentiate more confident haplotypes. The PHASE software is suitable for genetic distances of 100 cM or less. The probability values for the chromosomes with uncertain phase ranged form 0.51 to 0.65 for both the groups; these chromosomes accounted for only 2.07% of the control and 2.60% of the patient chromosomes. The haplotypes are shown in FIG. 2. The haplotypes 21_G_C and 23_G_T were the most frequent in the patient population. The odds of patients rather than controls having 21_G_C was 2.45 with 99% CI=(1.58, 3.94) [Likelihood $\chi^2$=27.92, df=1, p=0.00001] and 1.38 with 95% CI=(1.01, 1.87) [Likelihood $\chi^2$=4.21, df=1, p=0.04] for cohort A and B respectively. Similarly, the odds of patients rather than controls having 23_G_T was 2.64 with 99% CI=(1.51, 4.59) [Likelihood $\chi^2$=21.77, df=1, p=0.00001] and 3.55 with 99% CI=(2.00, 6.29) [Likelihood $\chi^2$=37.22, df=1, p=0.00001] for cohort A and cohort B respectively. These results suggest that 21_G_C (in cohort A) and 23_G_T (in both cohorts) are risk/susceptibility haplotypes and are positively associated with asthma. On the other hand, the haplotypes 22_G_C and 24_G_C were the most frequent in the control population. The odds (OR) of patients rather than controls having 22_G_C was 0.18 with 99% CI=(0.10, 0.31) [Likelihood $\chi^2$=35.32, df=1, p=0.00001] and 0.33 with 99% CI=(0.20, 0.54) [Likelihood $\chi^2$=72.28, df=1, p=0.00001] for cohort A and B respectively. Similarly, the odds of patients rather than controls having 24_G_C was 0.48 with 95% CI=(0.24, 0.98) [Likelihood $\chi^2$=4.28, df=1, p=0.038] and 0.28 with 99% CI= (0.12, 0.68) [Likelihood $\chi^2$=16.01, df=1, p=0.00001] for cohort A and B respectively. These results suggest that 22_G_C (in both cohorts) and 24_G_C (in cohort B) are protective haplotypes and are negatively associated with asthma.

Alternative embodiments of the invention can be envisaged by those skilled in the art from the information contained herein. All such alternative embodiments are intended to lie within the scope of this application.

The reader's attention is directed to all papers and documents which are filed concurrently with this specification, and the contents of all such papers and documents are incorporated herein by reference.

All the features disclosed in this specification (including any accompanying claims, abstract and drawing), and/or all of the steps or any method or process so disclosed, may be combined in any combination, except combination where at least some of such features and/or steps are mutually exclusive.

Each feature disclosed in this specification (including any accompanying claims, abstract and drawings), may be replaced by alternative features serving the same or equivalent or similar purpose, unless expressly stated otherwise. Thus, unless expressly slated otherwise, each feature disclosed is one example only of a generic series of equivalent or similar features.

The invention is not restricted to the details of the embodiments. This invention extends to any novel one, or any novel combination, or the features disclosed in this specification (including any accompanying claims, abstract and drawings), or to any novel one, or any novel combination, of the steps of any method or process so disclosed.

Although the present invention has been described in some detail by way of illustration and example for purposes of clarity and understanding, it will be apparent that certain changes and modifications may be practiced within the scope of the appended claims.

TABLE 1

Primer details for PCR of various loci

| Primer | No. of bases | Sequence | Amplified product size |
|---|---|---|---|
| $(CT)_n(CA)_m$ FP (FAM labeled) | 20 bases | 5' CCC GAG TAA GGC GAG CAT CT 3' (SEQ ID NO: 4) | 363 bps |
| $(CT)_n(CA)_m$ RP | 19 bases | 5' TTA AGC CCG GGA GGT CAA G 3' (SEQ ID NO: 5) | |
| −800G/A FP | 20 bases | 5' CCC GGC TCC ATT TCC AGG TG 3' (SEQ ID NO: 6) | 388 bps |
| −800G/A RP | 20 bases | 5' TGC TCT TGA CCA CTG TGC CA 3' (SEQ ID NO: 7) | |
| −509C/T FP | 20 bases | 5' CAG ACT CTA GAG ACT GTC AG 3' (SEQ ID NO: 8) | 418 bps |
| −509C/T RP | 19 bases | 5' GTC ACC AGA GAA AGA GGA C 3' (SEQ ID NO: 9) | |
| −988C1A FP | 20 bases | 5' TGC GAG CTT GCA GGC TAT GG 3' (SEQ ID NO: 10) | 232 bps |
| −988C/A RP | 20 bases | 5' GGA GCA GCA GGC CGA TCT CC 3' (SEQ ID NO: 11) | |
| 788C/T FP | 19 bases | 5' TTC CCT CGA GGC CCT CCT A 3' (SEQ ID NO: 12) | 294 bps |
| 788C/T RP | 20 bases | 5' GCC GCA GCT TGG ACA GGA TC 3' (SEQ ID NO: 13) | |

TABLE 2

Allele Frequencies of $(CT)_n(CA)_m$ polymorphism in TGFβ1 gene.

| | Number of individuals | | | | | | | | | |
|---|---|---|---|---|---|---|---|---|---|---|
| $(CT)_n(CA)_m$ | Cohort A | | | | | Cohort B | | | | |
| Allele | Cases (%) | Controls (%) | OR | 99% CI | p-value[a] | Cases (%) | Controls (%) | OR | 99% CI | p-value[b] |
| 19 | 1 (0.27) | 1 (0.27) | | | | — | — | | | |
| 20 | 1 (0.27) | 8 (2.14) | | | | 1 (0.24) | 2 (0.53) | | | |
| 21 | 183 (48.93) | 96 (25.67) | 2.77 | 1.85, 4.16 | 0.0000 | 183 (43.78) | 120 (31.58) | 1.69 | 1.15, 2.47 | 0.0003 |
| 22 | 44 (11.76) | 151 (40.37) | 0.20 | 0.12, 0.32 | 0.0000 | 59 (14.11) | 129 (33.95) | 0.32 | 0.20, 0.50 | 0.0000 |
| 23 | 116 (31.02) | 62 (16.58) | 2.26 | 1.43, 3.58 | 0.0000 | 124 (29.67) | 49 (12.89) | 2.85 | 1.76, 4.6 | 0.0000 |
| 24 | 27 (7.22) | 51 (13.64) | 0.49 | 0.26, 0.94 | 0.0038 | 45 (10.77) | 70 (18.42) | 0.53 | 0.31, 0.90 | 0.0020 |
| 25 | 2 (0.53) | 5 (1.34) | | | | 6 (1.44) | 10 (2.63) | | | |

(For Bonferroni correction,
[a] α = 0.007 and
[b] α = 0.008)
Numbers in parentheses indicate the frequency {%}

TABLE 3

Distribution of Allele and Genotype Frequencies for −800G/A and −509C/T polymorphisms in two cohorts studied.

| | Number of Individuals | | | | | | | | | |
|---|---|---|---|---|---|---|---|---|---|---|
| | Cohort A | | | | | Cohort B | | | | |
| | Patients | Controls | OR | 99% CI | p-value | Patients | Controls | OR | 99% CI | p-value |
| Alleles | | | | | | | | | | |
| −509 | | | | | | | | | | |
| C | 232 (62.03) | 265 (70.86) | 0.67 | 0.45, 1.00 | 0.01 | 243 (58.13) | 287 (75.53) | 0.45 | 0.30, 0.67 | 0.0000 |
| T | 142 (37.97) | 109 (29.14) | | | | 175 (41.87) | 93 (24.47) | | | |
| −800 | | | | | | | | | | |
| A | 39 (10.43) | 25 (6.68) | | | N.S. | 24 (5.74) | 20 (5.26) | | | N.S. |
| G | 335 (89.57) | 349 (93.32) | | | | 394 (94.26) | 360 (94.74) | | | |
| Genotypes | | | | | | | | | | |
| −509 | | | | | | | | | | |
| CC | 64 (34.22) | 94 (50.27) | 0.51 | 0.30, 0.89 | 0.0016 | 73 (34.93) | 112 (58.95) | 0.37 | 0.22, 0.64 | 0.0000 |
| CT | 104 (55.61) | 77 (41.18) | 1.79 | 1.04, 3.07 | 0.0051 | 97 (46.41) | 63 (33.16) | 1.74 | 1.02, 2.98 | 0.0068 |
| TT | 19 (10.16) | 16 (8.56) | | | | 39 (18.66) | 15 (7.89) | | | |
| −800 | | | | | | | | | | |
| AA | 0 (0.00) | 1 (0.53) | | | N.S. | 0 (0.00) | 0 (0.00) | | | N.S. |
| GA | 39 (20.86) | 23 (12.30) | | | | 24 (11.48) | 20 (10.53) | | | |
| GG | 148 (79.14) | 163 (87.17) | | | | 185 (88.52) | 170 (89.47) | | | |

Numbers in parentheses indicate the frequency {%},
N.S.—Non-significant

TABLE 4

Multiple logistic regression analysis of the TGFβ1 polymorphisms for risk of asthma.

| | Cohort A | | | Cohort B | | |
|---|---|---|---|---|---|---|
| Variable | LR $\chi^2$ | df | p-value | LR $\chi^2$ | df | p-value |
| MODEL 1 | | | | | | |
| $(CT)_n(CA)_m$ genotype | 64.89 | 17 | 0.00001 | 41.31 | 15 | 0.0003 |
| −800 genotype | 7.49 | 2 | 0.02 | 0.076 | 1 | 0.78 |
| −509 genotype | 8.59 | 2 | 0.013 | 5.56 | 2 | 0.062 |
| Age | 10.57 | 1 | 0.001 | 9.15 | 1 | 0.002 |
| Sex | 0.77 | 1 | 0.38 | 6.13 | 1 | 0.013 |
| MODEL 2 | | | | | | |
| $(CT)_n(CA)_m$ genotype | 79.95 | 17 | 0.00001 | 50.76 | 17 | 0.0001 |
| −800 genotype | 6.02 | 2 | 0.049 | 0.11 | 1 | 0.73 |
| −509 genotype | 7.13 | 2 | 0.028 | 10.88 | 2 | 0.004 |

Model 1: There was controlling for age and sex;
Model 2: There was no controlling for age and sex.

TABLE 5

Serum TGFβ1 levels in context of Alleles, Genotypes and Haplotypes.

| | Number | Log TGFβ1 levels (±SE) | F-ratio | DF | P-value |
|---|---|---|---|---|---|
| $(CT)_n(CA)_m$ Alleles | | | | | |
| 21 | 50 | 1.73 (±0.03) | 4.59 | 3 | 0.004 |
| 22 | 33 | 1.59 (±0.04) | | | |
| 23 | 37 | 1.76 (±0.04) | | | |
| 24 | 15 | 1.62 (±0.06) | | | |
| −509 C/T Genotype | | | | | |
| CC | 28 | 1.62 (±0.06) | 9.63 | 2 | 0.0002 |
| CT | 46 | 1.79 (±0.05) | | | |
| TT | 7 | 2.24 (±0.13) | | | |
| Haplotype | | | | | |
| 22_G_C/22_G_C | 5 | 1.41 (±0.13) | 6.87 | 2 | 0.0019 |
| 22_G_C/Non22_G_C | 20 | 1.61 (±0.07) | | | |
| Non22_G_C/Non22_G_C | 47 | 1.83 (±0.04) | | | |
| 23_G_T/23_G_T | 3 | 2.09 (±0.15) | 4.77 | 2 | 0.01 |
| 23_G_T/Non23_G_T | 23 | 1.79 (±0.05) | | | |
| Non23_G_T/Non23_G_T | 46 | 1.66 (±0.04) | | | |

TABLE 6

Demographic profile of the patient and the control groups.

| | Patients | | Controls | |
|---|---|---|---|---|
| | Cohort A | Cohort B | Cohort A | Cohort B |
| Mean Age: | 28.42 (±0.97) | 34.22 yrs (±1.01) | 24.01 yrs (±0.95) | 29.35 yrs (±1.00) |
| Sex ratio (M Vs F): | 0.52:0.48 | 0.53:0.46 | 0.58:0.41 | 0.56:0.43 |
| Familial history of Asthma/Atopy: | All | All | None | None |

TABLE 6-continued

Demographic profile of the patient and the control groups.

| | Patients | | Controls | |
| --- | --- | --- | --- | --- |
| | Cohort A | Cohort B | Cohort A | Cohort B |
| Smoking History: | None | None | None | None |
| % Reversibilty from baseline FEV1 (after $\beta_2$-agonist usage): | >15% | >15% | ND | ND |
| Log Mean Total serum IgE (IU/ml): | 2.85 ± 0.07 | 2.87 ± 0.04 | 2.41 ± 0.07 | 2.40 ± 0.05 |
| Self reported history of allergies: | All | All | None | None |

Parenthesis contains the values for standard error (SE).
'ND' denotes that the test is not done.

REFERENCES

1. Abney M, Ober C, McPeek M S (2002) Quantitative-trait homozygosity and association mapping and empirical genomewide significance in large, complex pedigrees: fasting serum-insulin level in the Hutterites. Am J Hum Genet 70:920-34.
2. Alam R et al (1994) Transforming growth factor beta abrogates the effects of hematopoietins on eosinophils and induces their apoptosis. J Exp Med 179: 1041-1045.
3. Altshuler D, Kruglyak L, Lander E (1998) Genetic polymorphisms and disease. N Engl J Med 338:1626.
4. Anonymous. National Asthma Education and Prevention Program. Expert Panel Report, Guidelines for the Diagnosis and Management of Asthma Update on Selected Topics—2002. J Allergy Clin Immunol 2002; 110:S141-S219.
5. Aubert J D, Dalal B I, Bai T R et al (1994) Transforming growth factor β1 gene expression in human airways. Thorax 49:225-232.
6. Babron M C, Selinger-Leneman H, Dizier M H, Clerget-Darpoux F (2001) Homogeneity of asthma genome scan results. Genet Epidemiol 21 Suppl 1:S44-8.
7. Barringer K J, Orgel L, Wahl G, Gingeras T R (1990) Blunt-end and single-strand ligations by *Escherichia coli* ligase: influence on an in vitro amplification scheme. Gene 89:117-22.
8. Baron M (2001) The search for complex disease genes: fault by linkage or fault by association? Mol Psychiatry 6:143-9.
9. Barnes P J (2001) Th2 cytokines and asthma: an introduction. Respir Res 2:64-5.
10. Barnes K C (1999) Gene-environment and gene-gene interaction studies in the molecular genetic analysis of asthma and atopy. Clin Exp Allergy 29 Suppl 4:47-51.
11. Barnes K C, Neely J D, Duffy D L, Freidhoff L R, Breazeale D R, Schou C, Naidu R P, et al (1996) Linkage of asthma and total serum IgE concentration to markers on chromosome 12q: evidence from Afro-Caribbean and Caucasian populations. Genomics 37:41-50.
12. Ben-Asouli Y, Banai Y, Pel-Or Y, Shir A, Kaempfer R (2002) Human interferon-gamma mRNA autoregulates its translation through a pseudoknot that activates the interferon-inducible protein kinase PKR. Cell 108:221-32.
13. Bleecker E R, Postma D S, Meyers D A (1997) Evidence for multiple genetic susceptibility loci for asthma. Am J Respir Crit Care Med 156:S113-6.
14. Blumenthal M N, Amos D B (1987) Genetic and immunologic basis of atopic responses. Chest 91:176S-184S.
15. Blumenthal M N, Langefeld C D (2004) A genome-wide search for allergic response (atopy) genes in three ethnic groups: Collaborative Study on the Genetics of asthma. Hum Genet 114(2):157-164.
16. Blumenthal M N, Ober C (2004) Genome scan for loci linked to mite sensitivity: the Collaborative Study on the Genetics of Asthma (CSGA). Genes Immun 5(3):226-231.
17. Bodmer W F (1987) The human genome sequence and the analysis of multifactorial traits. Ciba Found Symp 130: 215-28.
18. Breslow J L (1988) Apolipoprotein genetic variation and human disease. Physiol Rev 68:85-132.
19. Buckova I, Izakovicova L H, Vacha J TGFβ1 gene polymorphisms. Allergy Net 1236-1237.
20. Caraballo L R, Hernandez M (1990) HLA haplotype segregation in families with allergic asthma. Tissue Antigens 35:182-6.
21. Cargill M, Altshuler D, Ireland J. Sklar P, Ardlie K, Patil N, Shaw N, et al (1999) Characterization of single-nucleotide polymorphisms in coding regions of human genes. Nat Genet 22:231-8.
22. Carriere K C, Kochar S C (2000): Comparing sub-survival functions in a competing risks model Lifetime Data Anal.: 6(1):85-97.
23. Chakraborty A K and Hodgson C P. Role of far upstream repressor elements controlling proto-Ha-ras gene transcription. Biochem Biophys Res Commun 1998; 252:716-722.
24. Chang C, Bowman J L, DeJohn A W, Lander E S, Meyerowitz E M (1988) Restriction fragment length polymorphism linkage map for *Arabidopsis thaliana*. Proc Natl Acad Sci USA 85:6856-60.
25. Christie L, Hine R J, Parker J G, Burks W (2002). Food allergies in children affect nutrient intake and growth. J Am Diet Assoc. 102 (11):1648-51.
26. Cohen D, Cohen O, Marcadet A, Massart C, Lathrop M, Deschamps I, Hors J, et al (1984) Class II HLA-DC betachain DNA restriction fragments differentiate among HLA-DR2 individuals in insulin-dependent diabetes and multiple sclerosis. Proc Natl Acad Sci USA 81:1774-8.
27. Cookson W O, Young R P, Sandford A J, Moffatt M F, Shirakawa T, Sharp P A, Faux J A, et al (1992) Maternal inheritance of atopic IgE responsiveness on chromosome 11q. Lancet 340:381-4.
28. Cookson W (1999) The alliance of genes and environment in asthma and allergy. Nature 402:B5-11.
29. Dunning A M, Ellis P D, McBride S, Kirschenlohr H L, Healey C S, Kemp P R, et al. A transforming growth factor beta1 signal peptide variant increases secretion in vitro and is associated with increased incidence of invasive breast cancer. Cancer Res. 2003; 63(10):2610-2615.
30. Duffy D L (1997) Genetic epidemiology of asthma. Epidemiol Rev 19:129-43.
31. Elias J A, Zhu Z, Chupp G, Homer R J. Airway remodeling in asthma. J Clin Invest 1999; 104:1001-1006.
32. Erlich H A (eds), Freeman Press, N.Y., N.Y., 1992); PCR Protocols: A Guide to Methods and Applications (eds. Innis, et al., Academic Press, San Diego, Calif., 1990.
33. Friedhoff P, Hahn M, Wolfes H, Pingoud A (1993) Quantitative polymerase chain reaction with oligodeoxynucleotide ligation assay/enzyme-linked immunosorbent assay detection. Anal Biochem 215:9-16.
34. Fujii D, Brissenden J. E, Derynck R, Francke U (1986) Transforming growth factor beta gene maps to human chromosome 19 long arm and to mouse chromosome 7. Somat Cell Mol Genet 12:281-288
35. de Gouyon B, Melanitou E, Richard M F, Requarth M, Hahn I H, Guenet J L, Demenais F, et al (1993) Genetic analysis of diabetes and insulitis in an interspecific cross of the nonobese diabetic mouse with Mus spretus. Proc Natl Acad Sci USA 90:1877-81.
36. Ghosh B, Genetic studies of atopic asthma in Indian Population, In: International Symposium on Genes, Evolution and Complex disease, February, 2005, at NCBS, Banglore.
37. Ghosh B. Genetics of Asthma In: Workshop on Genetic Epidemiological Methods for dissection of complex human traits, Organized by TG-ISI, Kolkota and University of Pittsburgh, USA, December 2004.
38. Grainger D J, Heathcote K, Chiano M, Sneider H, Kemp P R et al Genetic control of the circulating concentration of transforming growth factor β1. Hum Mol Gen 8:93-97
39. Hacia J G, Fan J B, Ryder O, Jin L, Edgemon K, Ghandour G, Mayer R A, et al (1999) Determination of ancestral alleles for human single-nucleotide polymorphisms using high-density oligonucleotide arrays. Nat Genet 22:164-7.
40. Hansen G, McIntire J J, Yeung V P, Berry G, Thorbecke G J, Chen L, DeKruyff R H, Umetsu D T (2000) CD4+ Th cells engineered to produce latent TGFb1 reverse allergen-induced airway hyperreactivity and inflammation. J Clin Invest 105:61-70
41. Hefferon W T, Groman D J, Yurk E C, Garry R C (2004) A variable dinucleotide repeat in the CFTR gene contributes to phenotype diversity by forming RNA secondary structures that alter splicing. PNAS 101(10):3504-3509.
42. Heinzmann A, Grotherr P, Jerkic S P, Lichtenberg A, Braun S, Kruse S, Forster J, et al (2000) Studies on linkage and association of atopy with the chromosomal region 12q13-24. Clin Exp Allergy 30:1555-61.
43. Hill S, Herlaar E, Le Cardinal A, van Heeke G, Nicklin P (1999) Homologous human and murine antisense oligonucleotides targeting stat6. Functional effects on germline cepsilon transcript. Am J Respir Cell Mol Biol 21:728-37.
44. Hirschhorn J N, Sklar P, Lindblad-Toh K, Lim Y M, Ruiz-Gutierrez M, Bolk S, Langhorst B, et al (2000) SBE-TAGS: an array-based method for efficient single-nucleotide polymorphism genotyping. Proc Natl Acad Sci USA 97:12164-9.
45. Hobbs K, Negri J, Klinnert M, Rosenwasser L, Borish L (1998) Interleukin-10 and transforming growth factor-β promoter polymorphisms in allergies and asthma. Am J Respir Crit Care Med 158: 1958-1962
46. Holbert S, Denghien I, Kiechle T, Rosenblatt A, Wellington C, Hayden M R, et al. The Gln-Ala repeat transcriptional activator CA150 interacts with huntingtin:neuropathologic and genetic evidence for a role in Huntington's disease pathogenesis. Proc Natl Acad Sci USA. 2001:98 (4):1811-18166.
47. Julier C, de Gouyon B, Georges M, Guenet J L, Nakamura Y, Avner P. Lathrop G M (1990) Minisatellite linkage maps in the mouse by cross-hybridization with human probes containing tandem repeats. Proc Natl Acad Sci USA 87:4585-9.
48. Kreutz R, Hubner N, James M R, Bihoreau M T, Gauguier D, Lathrop G M, Ganten D, et al (1995), Dissection of a quantitative trait locus for genetic hypertension on rat chromosome 10. Proc Natl Acad Sci USA 92:8778-82.
49. Kwoh D Y, Davis G R, Whitfield K M, Chappelle H L, DiMichele L J, Gingeras T R (1989) Transcription-based amplification system and detection of amplified human immunodeficiency virus type 1 with a bead-based sandwich hybridization format. Proc Natl Acad Sci USA 86:1173-7.
50. Lander E S, Botstein D (1986) Strategies for studying heterogeneous genetic traits in humans by using a linkage map of restriction fragment length polymorphisms. Proc Natl Acad Sci USA 83:7353-7.
51. Lander E S (1993) Finding similarities and differences among genomes. Nat Genet 4:5-6.
52. Lathrop G M, Lalouel J M, Julier C, Ott J (1984) Strategies for multilocus linkage analysis in humans. Proc Natl Acad Sci USA 81:3443-6.
53. Levitt R C (1994) Molecular-genetic methods for mapping disease genes. Am J Respir Crit Care Med 150:S94-9.
54. Longo D R, Johnson J C, Kruse R L, Brownson R C, Hewett J E (2001): A prospective investigation of the impact of smoking bans on tobacco cessation and relapse. Tob Control, September; 10(3):267-72.
55. Massague J (1990) The transforming growth factor β family. Annu Rev Cell Biol 6:597-641.
56. Mattila P, Korpela J, Tenkanen T, Pitkanen K (1991) Fidelity of DNA synthesis by the *Thermococcus litoralis* DNA polymerase—an extremely heat stable enzyme with proofreading activity. Nucleic Acids Res 19:4967-73.
57. Minshall E M, Leung D Y M, Song Y L, Cameron 1, Ernst P, Hamid Q (1997) Eosinophil associated TGFβ1 mRNA expression and airway fibrosis in bronchial asthma. Am J Respir Cell Mol Biol 17:326-333
58. Mokdad-Gargouri R, Belhadj K, Gargouri A (2001) Translational control of human p53 expression in yeast mediated by 5'-UTR-ORF structural interaction. Nucleic Acids Res 29:1222-7.
59. Mukawa A, Kamitsuma Y, Tsunekawa S, Tanaka N (1989): Report on a long-term trial of CYBEST Model 2 for prescreening for squamous cell carcinoma of the uterine cervix Anal Cell Pathol. August; 1(4):225-33.
60. Nakao A, Miike S, Hatano M, Okumura K, Tokuhisa T, Ra C, et al. Blockade of transforming growth factor beta/Smad signaling in T cells by overexpression of Smad7 enhances antigen-induced airway inflammation and airway reactivity. J Exp Med. 2000; 192(2):151-158.
61. Nagarkatti R, Rao C B, Rishi J P, Chetiwal R, Shandilya V, Vijayan V, et al. (2002) Association of IFNG gene polymorphism with asthma in the Indian population. J Allergy Clin Immunol 2002; 110:410-412.
62. Nagpal K, Sharma S, B-Rao C, Nahid S, Niphadkar P V, Sharma S K, Ghosh B (2005) TGFbeta1 haplotypes, and asthma in Indian populations. J Allergy Clin Immunol 115: 527-533.

63. Nagpal K, Sharma S, B-Rao C, Nahid S, Niphadkar P V, Sharma S K, Ghosh B (2005) TGFbeta1 haplotypes and asthma in Indian populations. In: "Biotech 2004" Oct. 18-21, 2004, New Delhi.

64. Nakao A, Miike S, Hatano M, Okumura K, Tokuhisa T, Ra C, Iwamoto I (2000): Blockade of transforming growth factor b/Smad signaling in T cells by overexpression of Smad7 enhances antigen-induced airway inflammation and airway reactivity. J Exp Med 192:151-158

65. Ober C, Tsalenko A, Parry R, Cox N J (2000) A second-generation genomewide screen for asthma-susceptibility alleles in a founder population. Am J Hum Genet 67:1154-62.

66. Oberle I, Heilig R. Moisan J P, Kloepfer C, Mattei G M, Mattei J F, Boue J, et al (1986) Genetic analysis of the fragile-X mental retardation syndrome with two flanking polymorphic DNA, markers. Proc Natl Acad Sci USA 83:1016-20.

67. Ohno I, Nitta Y, Yamouchi K, Hoshi H et al (1996) Transforming growth factor β1 (TGFβ1) gene expression by eosinophils in asthmatic airway inflammation. Am J Respir Cell Mol Biol 15:404-409.

68. Orita M, Iwahana H, Kanazawa H, Hayashi K, Sekiya T (1989) Detection of polymorphisms of human DNA by gel electrophoresis as single-strand conformation polymorphisms. Proc Natl Acad Sci USA 86:2766-70.

69. Paul W E (1997) Interleukin 4: signalling mechanisms and control of T cell differentiation. Ciba Found Symp 204:208-16; discussion 216-9.

70. Piacquadio D J, Chen D M, Farber H F, Fowler J F Jr, Glazer S D, Goodman J J, Hruza L L, Jeffes E W, Ling M R, Phillips T J, Rallis T M, Scher R K, Taylor C R, Weinstein G D (2004): Photodynamic therapy with aminolevulinic acid topical solution and visible blue light in the treatment of multiple actinic keratoses of the face and scalp: investigator-blinded, phase 3, multicenter trials. Arch Dermatol.; 140(1): 41-6.

71. Pulleyn L J, Newton R, Adcock I M, Barnes P J. TGFbeta1 allele association with asthma severity. Hum Genet. 2001; 109(6):623-627.

72. Redington A E, Madden J, Frew A J, Djukanovic R. Roche W R, Holgate S T et al. Transforming growth factor-beta 1 in asthma. Measurement in bronchoalveolar lavage fluid. Am J Respir Crit Care Med 1997; 156:642-647.

73. Reich D E, Cargill M, Bolk S, Ireland J, Sabeti P C, Richter D J, Lavery T, et al (2001) Linkage disequilibrium in the human genome. Nature 411:199-204.

74. Rothenburg S, Koch-Nolte F, Rich A, Haag F (2001) A polymorphic dinucleotide repeat in the rat nucleolin gene forms Z-DNA and inhibits promoter activity. Proc Natl Acad Sci USA 98:8985-90.

75. Sachidanandam R, Weissman D, Schmidt S C, Kakol J M, Stein L D, Marth G, Sherry S, et al (2001) A map of human genome sequence variation containing 1.42 million single nucleotide polymorphisms. Nature 409:928-33.

76. Sambrook et al., Molecular Cloning, A Laboratory Manual, 2nd Ed., CSHP, New York 1989.

77. Saiki R K, Bugawan T L, Horn G T, Mullis K B, Erlich H A (1986) Analysis of enzymatically amplified beta-globin and HLA-DQ alpha DNA with allele-specific oligonucleotide probes. Nature 324:163-6.

78. Sharma S, Nagarkatti R, B-Rao C, Niphadkar P V, Vijayan V, Sharma S K, et al. A_16_C haplotype in FcεRIβ gene confers higher risk for atopic asthma in Indian population. Clin. Genet 2004: 66: 417-425.

79. Sherman M A, Secor V H, Brown M A (1999) IL-4 preferentially activates a novel STAT6 isoform in mast cells. J Immunol 162:2703-8.

80. Shivastava A, K Calame (1994) An analysis of genes regulated by the multi-functional transcriptional regulatory Yin-Yang 1. Nucleic Acids Res 24:5151-5155

81. Silverman E S, Palmer L J, Subramaniam V, Hallock A, Mathew S, Vallone J, et al. Transforming growth factor-beta1 promoter polymorphism C-509T is associated with asthma. Am J Respir Crit Care Med 2004; 169(2):214-219.

82. Sorensen G, Emmons K, Stoddard A M, Linnan L, Avrunin J (2002): Do social influences contribute to occupational differences in quitting smoking and attitudes toward quitting? Am J Health Promot. January-February; 16(3): 135-41.

83. Stephens M, Donnelly P (2003): A comparison of bayesian methods for haplotype reconstruction from population genotype data. Am J Hum Genet. November 73:1162-9.

84. Stephens M, Smith N J, Donnelly P. A new statistical method for haplotype reconstruction from population data. Am J Hum Genet 2001; 68:978-989.

85. Taylor A, Verhagen J, Akdis C A, Akdis M. T regulatory cells in allergy and health: a question of allergen specificity and balance. Int Arch Allergy Immunol 2004; 135(1):73-82.

86. Tay A H, Tan E C, Chew F T, Goh D L, Shek L P, Lee B W (1999) Ethnic differences in genetic susceptibility to atopy and asthma. Asian Pac J Allergy Immunol 17:239-42.

87. Texereau J, Marullo S, Hubert D, Coste J, Dusser D J, Dall'Ava-Santucci J, Dinh-Xuan A T. Nitric oxide synthase 1 as a potential modifier gene of decline in lung function in patients with cystic fibrosis. Thorax 2004; 59:156-158.

88. Thomas N S, Wilkinson J, Holgate S T (1997) The candidate region approach to the genetics of asthma and allergy. Am J Respir Crit Care Med 156:S144-51.

89. Tsunawaki S, Sporn M B, Ding A, Nathan C (1998) Deactivation of macrophages by transforming growth factor beta. Nature 334:260-262.

90. WO0208468 (2001). Diagnostic polymorphisms for the TGFbeta1 promoter.

91. Xu J, Wiesch D G, Meyers D A (1998) Genetics of complex human diseases: genome screening, association studies and fine mapping. Clin Exp Allergy 28 Suppl 5:1-5; discussion 26-8.

92. Xu J, Meyers D A, Ober C, Blumenthal M N, Mellen B, Barnes K C, King R A, et al (2001) Genomewide screen and identification of gene-gene interactions for asthma-susceptibility loci in three U.S. populations: collaborative study on the genetics of asthma. Am J Hum Genet 68:1437-46.

93. Zak N B, Shifman S, Shalom A, Darvasi A. Population-based gene discovery in the post-genomic era. Drug Discov Today 2001; 6:1111-1115.

94. Zuany-Amorim C, Sawicka E, Manlius C, Le Moine A, Brunet L R, Kemeny D M, et al. Suppression of airway eosinophilia by killed *Mycobacterium vaccae*-induced allergen-specific regulatory T-cells. Nat Med 2002; 8:625-9.

We claim:

1. An isolated human Transforming Growth Factor Beta1 (TGFβ1)-encoding nucleic acid comprising SEQ ID NO: 1, wherein the nucleotide content of positions 77-122 of SEQ ID NO: 1 comprises CA and CT dinucleotides and the number of said CA and CT dinucleotides is 19, 20, 21, 23, 24 or 25.

2. The isolated nucleic acid according to claim 1, wherein the number of said CA and CT dinucleotides is 23, further comprising SEQ ID NO: 2 wherein the nucleotide content of position 326 of SEQ ID NO: 2 comprises a G nucleotide and further comprising SEQ ID NO: 3 wherein the nucleotide content of position 229 of SEQ ID NO: 3 comprises a T nucleotide and wherein the sequence of the nucleic acid is indicative of a human subject's susceptibility to asthma.

3. The isolated nucleic acid of claim 1 further comprising SEQ ID NO: 3 wherein the nucleotide content of position 229 of SEQ ID NO: 3 comprises a T nucleotide.

4. The isolated nucleic acid of claim 1 further comprising SEQ ID NO: 2, wherein the nucleotide content of position 326 of SEQ ID NO: 2 comprises an A nucleotide.

5. The isolated nucleic acid of claim 1 further comprising SEQ ID NO: 3, wherein the nucleotide content of position 229 of SEQ ID NO: 3 comprises a T nucleotide and SEQ ID NO: 2 wherein the nucleotide of position 326 of SEQ ID NO: 2 comprises an A nucleotide.

6. The isolated nucleic acid according to any one of claim 1, 3, 4 or 5 wherein the nucleic acid is a pharmacogenetic marker for predicting or detecting a human subject's susceptibility to asthma.

7. The isolated nucleic acid of claim 1, wherein the number of said CA and CT dinucleotides is selected from the group consisting of 21 and 23, and wherein the number of said CA and CT dinucleotides is indicative of an increased risk of asthma.

8. The isolated nucleic acid of claim 1, wherein the number of said CA and CT dinucleotides is selected from the group consisting of 19, 20, 24 and 25, and wherein the number of said CA and CT dinucleotides is indicative of a decreased risk of asthma.

9. An isolated nucleic acid comprising a pharmacogenetic marker for detecting a TGFβ1-encoding nucleic acid correlated with an increased risk of asthma in a human of the Indian population, said marker comprising: SEQ ID NO: 1 wherein the nucleotide content of positions 77-122 of SEQ ID NO: 1 comprises CA and CT dinucleotides and the number of said CA and CT dinucleotides is 23; SEQ ID NO: 2 wherein the nucleotide content of position 326 of SEQ ID NO: 2 comprises an G nucleotide; and SEQ ID NO: 3 wherein the nucleotide content of position 229 of SEQ ID NO: 3 comprises a T nucleotide.

10. An isolated human Transforming Growth Factor Beta1 (TGFβ1)-encoding nucleic acid comprising SEQ ID NO: 1, wherein the nucleotide content of positions 77-122 of SEQ ID NO: 1 comprises CA and CT dinucleotides and the number of said CA and CT dinucleotides is 19, 20, 21, 23, 24 or 25, and wherein the nucleic acid further comprises SEQ ID NO: 3, wherein the nucleotide content of position 229 of SEQ ID NO: 3 comprises a T nucleotide or SEQ ID NO: 2 wherein the nucleotide of position 326 of SEQ ID NO: 2 comprises an A nucleotide.

* * * * *

SEQUENCE LISTING

<160> NUMBER OF SEQ ID NOS: 13

<210> SEQ ID NO 1
<211> LENGTH: 363
<212> TYPE: DNA
<213> ORGANISM: Homo sapiens
<220> FEATURE:
<221> NAME/KEY: DNA
<222> LOCATION: (1)..(363)
<223> OTHER INFORMATION: consist of CT/CA dinucleotides at 77 TO 122
      BASES

<400> SEQUENCE: 1
ttaagcccgg gaggtcaagg ttgcagtaaa ctatgatcgc tccactgcac tccagcctgg      60
gcaacagagc gagaccctgt ctctctctct ctctctctct ctctctctca cacacacaca     120
caaagaggga gacagcaggg tggacaaaag ccagaggtgc atgcactctg aagacaccaa     180
ccagcggagt ctgagatcag agggaagaca gagccaaaag ccaggcaaca aagatgagag     240
acataaaaca agaagaaccg taactggaaa tctcagaagc ccacacacag ctgggaagtg     300
agactccagg cctaaggcag atcggcacag ctgtcaacct gccagatgct ggccttagtg     360
ggg                                                                   363

<210> SEQ ID NO 2
<211> LENGTH: 388
<212> TYPE: DNA
<213> ORGANISM: Homo sapiens
<220> FEATURE:
<221> NAME/KEY: DNA
<222> LOCATION: (1)..(388)
<223> OTHER INFORMATION: consist of G/A polymorphism at nucelotide 326

<400> SEQUENCE: 2
cccggctcca tttccaggtg tggtcccagg acagctttgg ccgctgccag cttgcaggct      60
atggattttg ccatgtgccc agtagcccgg gcacccacca gctggcctgc cccacgtggc     120
ggcccctggg cagttggcga gaacagttgg cacgggcttt cgtgggtggt gggccgcagc     180
tgctgcatgg ggacaccatc tacagtgggg ccgaccgcta tcgcctgcac acagctgctg     240
gtggcaccgt gcacctggag atcggcctgc tgctccgcaa cttcgaccgc tacggcgtgg     300
agtgctgagg gactctgcct ccaacgtcac caccatccac accccggaca cccagtgatg     360
ggggaggatg gcacagtggt caagagca                                        388

<210> SEQ ID NO 3
<211> LENGTH: 418
<212> TYPE: DNA
<213> ORGANISM: Homo sapiens
<220> FEATURE:
<221> NAME/KEY: DNA
<222> LOCATION: (1)..(418)
<223> OTHER INFORMATION: consists of C/T polymorphism at nucleotide 229

<400> SEQUENCE: 3
cagactctag agactgtcag agctgacccc agctaaggca tggcaccgct tctgtccttt      60
ctaggacctc ggggtccctc tgggcccagt ttccctatct gtaaattggg gacagtaaat     120 gtatgggtc gcagggtgtt gagtgacagg aggctgctta gccacatggg aggtgctcag      180
taaaggagag caattcttac aggtgtctgc ctcctgaccc ttccatcctt caggtgtcct     240 gttgcccct cctcccactg acaccctccg gaggccccca tgttgacaga ccctcttctc      300

-continued

```
ctaccttgtt tcccagcctg actctccttc cgttctgggt cccctcctc tggtcggctc    360 ccctgtgtct catcccccgg attaagcctt ctccgcctgg tcctctttct ctggtgac     418
```

<210> SEQ ID NO 4
<211> LENGTH: 20
<212> TYPE: DNA
<213> ORGANISM: Artificial sequence
<220> FEATURE:
<221> NAME/KEY: Synthetic Oligonucleotide Primer
<222> LOCATION: (1)..(20)
<223> OTHER INFORMATION: Forward primer for SEQ ID No. 1 ((CT)n(CA)m Forward Primer)

<400> SEQUENCE: 4

```
ccccactaag gccagcatct                                                20
```

<210> SEQ ID NO 5
<211> LENGTH: 19
<212> TYPE: DNA
<213> ORGANISM: Artificial sequence
<220> FEATURE:
<221> NAME/KEY: Oligonucleotide Primer
<222> LOCATION: (1)..(19)
<223> OTHER INFORMATION: SEQ ID No. 1 ((CT)n(CA)m Reverse Primer)

<400> SEQUENCE: 5

```
ttaagcccgg gaggtcaag                                                 19
```

<210> SEQ ID NO 6
<211> LENGTH: 20
<212> TYPE: DNA
<213> ORGANISM: Artificial sequence
<220> FEATURE:
<221> NAME/KEY: Oligonucleotide primer
<222> LOCATION: (1)..(20)
<223> OTHER INFORMATION: Forward primer for SEQ ID No. 2 (-800G/A Forward Primer)

<400> SEQUENCE: 6

```
cccggctcca tttccaggtg                                                20
```

<210> SEQ ID NO 7
<211> LENGTH: 20
<212> TYPE: DNA
<213> ORGANISM: Artificial sequence
<220> FEATURE:
<221> NAME/KEY: Oligonucleotide primer
<222> LOCATION: (1)..(20)
<223> OTHER INFORMATION: Reverse primer for SEQ ID No. 2 (-800G/A Reverse Primer)

<400> SEQUENCE: 7

```
tgctcttgac cactgtgcca                                                20
```

<210> SEQ ID NO 8
<211> LENGTH: 20
<212> TYPE: DNA
<213> ORGANISM: Artificial sequence
<220> FEATURE:
<221> NAME/KEY: Oligonucleotide primer
<222> LOCATION: (1)..(20)
<223> OTHER INFORMATION: Forward primer for SEQ ID No. 3 (-509C/T Forward Primer)

<400> SEQUENCE: 8

```
cagactctag agactgtcag                                                20
```

-continued

```
<210> SEQ ID NO 9
<211> LENGTH: 19
<212> TYPE: DNA
<213> ORGANISM: Artificial sequence
<220> FEATURE:
<221> NAME/KEY: Oligonucleotide primer
<222> LOCATION: (1)..(19)
<223> OTHER INFORMATION: Reverse primer for SEQ ID No. 3 (-509C/T
      Reverse Primer)

<400> SEQUENCE: 9
gtcaccagag aaagaggac                                                19

<210> SEQ ID NO 10
<211> LENGTH: 20
<212> TYPE: DNA
<213> ORGANISM: Artificial sequence
<220> FEATURE:
<223> OTHER INFORMATION: -988C/A Forward Primer

<400> SEQUENCE: 10
tgccagcttg caggctatgg                                               20

<210> SEQ ID NO 11
<211> LENGTH: 20
<212> TYPE: DNA
<213> ORGANISM: Artificial sequence
<220> FEATURE:
<223> OTHER INFORMATION: -988C/A Reverse Primer

<400> SEQUENCE: 11
ggagcagcag gccgatctcc                                               20

<210> SEQ ID NO 12
<211> LENGTH: 19
<212> TYPE: DNA
<213> ORGANISM: Artificial sequence
<220> FEATURE:
<223> OTHER INFORMATION: 788C/T Forward Primer

<400> SEQUENCE: 12
ttccctcgag gccctccta                                                19

<210> SEQ ID NO 13
<211> LENGTH: 20
<212> TYPE: DNA
<213> ORGANISM: Artificial sequence
<220> FEATURE:
<223> OTHER INFORMATION: 788C/T Reverse Primer

<400> SEQUENCE: 13
gccgcagctt ggacaggatc                                               20
```